(12) United States Patent
Lerf et al.

(10) Patent No.: US 10,350,071 B2
(45) Date of Patent: Jul. 16, 2019

(54) COATED HEMI-PROSTHESIS IMPLANT

(71) Applicant: Mathys AG Bettlach, Bettlach (CH)

(72) Inventors: Reto Lerf, Langendorf (CH); Stefan Scheurer, Luterkofen (CH)

(73) Assignee: Mathys AG Bettlach, Bettlach (CH)

( * ) Notice: Subject to any disclaimer, the term of this patent is extended or adjusted under 35 U.S.C. 154(b) by 17 days.

(21) Appl. No.: 15/106,995

(22) PCT Filed: Nov. 18, 2014

(86) PCT No.: PCT/EP2014/074865
§ 371 (c)(1),
(2) Date: Jun. 21, 2016

(87) PCT Pub. No.: WO2015/096938
PCT Pub. Date: Jul. 2, 2015

(65) Prior Publication Data
US 2017/0000613 A1    Jan. 5, 2017

(30) Foreign Application Priority Data
Dec. 23, 2013  (DE) .......................... 10 2013 227 136

(51) Int. Cl.
*A61F 2/30*    (2006.01)
*A61F 2/38*    (2006.01)
(Continued)

(52) U.S. Cl.
CPC ............ *A61F 2/30* (2013.01); *A61F 2/30767* (2013.01); *A61F 2/3609* (2013.01);
(Continued)

(58) Field of Classification Search
CPC .............. A61F 2/30767; A61F 2/3662; A61F 2002/30275; A61F 2/28; A61F 2/34; A61F 2/36; A61F 2/30771
See application file for complete search history.

(56) References Cited

U.S. PATENT DOCUMENTS

| 4,166,292 A | * | 9/1979 | Bokros | ..................... A61F 2/38 623/21.18 |
| 5,011,515 A | * | 4/1991 | Frushour | .................. B22F 7/06 175/420.2 |

(Continued)

FOREIGN PATENT DOCUMENTS

| DE | 2921529 A1 | 12/1980 |
| DE | 202008015356 U1 | 3/2009 |

(Continued)

OTHER PUBLICATIONS

Int'l Prelim. Report on Patentability (English), Int'l Patent Appl. No. PCT/EP2014/074865, dated Nov. 18, 2014.

*Primary Examiner* — Alvin J Stewart
(74) *Attorney, Agent, or Firm* — Renaissance IP Law Group, LLP; David A. Crowther

(57) ABSTRACT

A hemi-prosthesis implant comprises a replacement-joint part with an articulation surface for tribological pairing with a joint surface of a natural joint counterpart. The articulation surface is embodied with a coating applied on a substrate. The substrate provides a relief for the adhesion of the coating. The relief may comprise one or more of a plurality of grooves, a plurality of teeth, a ribbing, and a roughened surface. The relief may be embodied entirely or partially outside the articulation surface. The replacement joint part may optionally comprise a ventilation feature, and the articulation surface may be formed by injection molding on the substrate. The hemi-prosthesis implant may be part of an implant set that includes both a hemi-prosthesis implant and a total prosthesis implant, either of which can be chosen intraoperatively.

20 Claims, 11 Drawing Sheets

(51) Int. Cl.
*A61F 2/36* (2006.01)
*A61F 2/40* (2006.01)
*A61F 2/42* (2006.01)

(52) U.S. Cl.
CPC .......... *A61F 2/3804* (2013.01); *A61F 2/3859* (2013.01); *A61F 2/4014* (2013.01); *A61F 2/4202* (2013.01); *A61F 2/3094* (2013.01); *A61F 2/4003* (2013.01); *A61F 2002/3007* (2013.01); *A61F 2002/30067* (2013.01); *A61F 2002/30332* (2013.01); *A61F 2002/30607* (2013.01); *A61F 2002/30616* (2013.01); *A61F 2002/30934* (2013.01); *A61F 2002/30973* (2013.01); *A61F 2002/3822* (2013.01); *A61F 2002/4207* (2013.01)

(56) References Cited

U.S. PATENT DOCUMENTS

| | | | | |
|---|---|---|---|---|
| 5,120,327 A | * | 6/1992 | Dennis | B22F 7/06 407/119 |
| 5,351,772 A | * | 10/1994 | Smith | E21B 10/5735 175/428 |
| 5,355,969 A | * | 10/1994 | Hardy | B23B 27/146 175/432 |
| 5,370,694 A | | 12/1994 | Davidson | |
| 5,564,511 A | * | 10/1996 | Frushour | B23B 27/146 175/431 |
| 6,290,726 B1 | * | 9/2001 | Pope | A61F 2/30767 623/18.11 |
| 6,709,463 B1 | * | 3/2004 | Pope | A61F 2/30767 623/23.51 |
| 8,556,981 B2 | * | 10/2013 | Jones | A61F 2/30907 623/18.11 |
| 8,603,181 B2 | * | 12/2013 | Pope | A61F 2/30767 623/17.14 |
| 2007/0299520 A1 | | 12/2007 | Trieu et al. | |
| 2013/0184820 A1 | * | 7/2013 | Schwartz | A61F 2/30756 623/14.12 |

FOREIGN PATENT DOCUMENTS

| | | |
|---|---|---|
| EP | 0608997 A1 | 8/1994 |
| EP | 2086471 B1 | 11/2010 |
| GB | 2491867 A | 12/2012 |
| WO | 2012154920 A1 | 11/2012 |

* cited by examiner

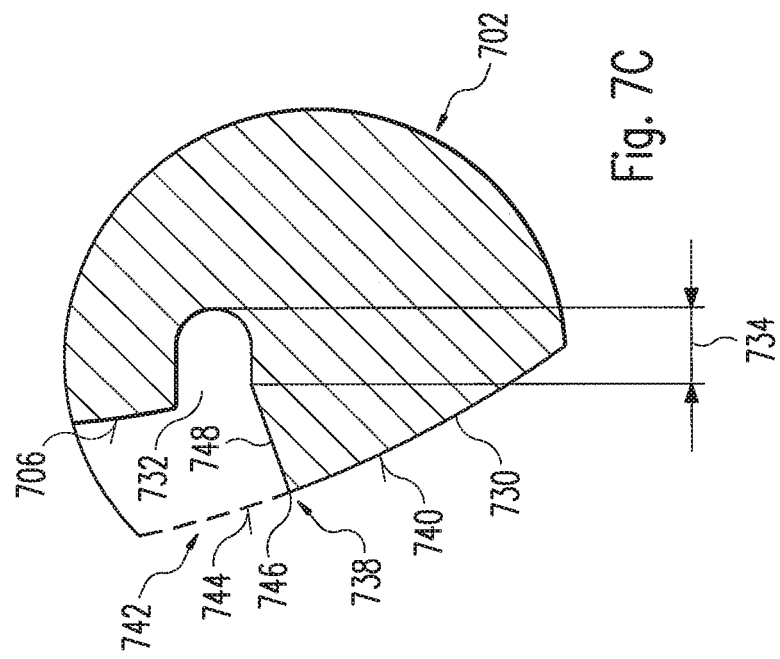
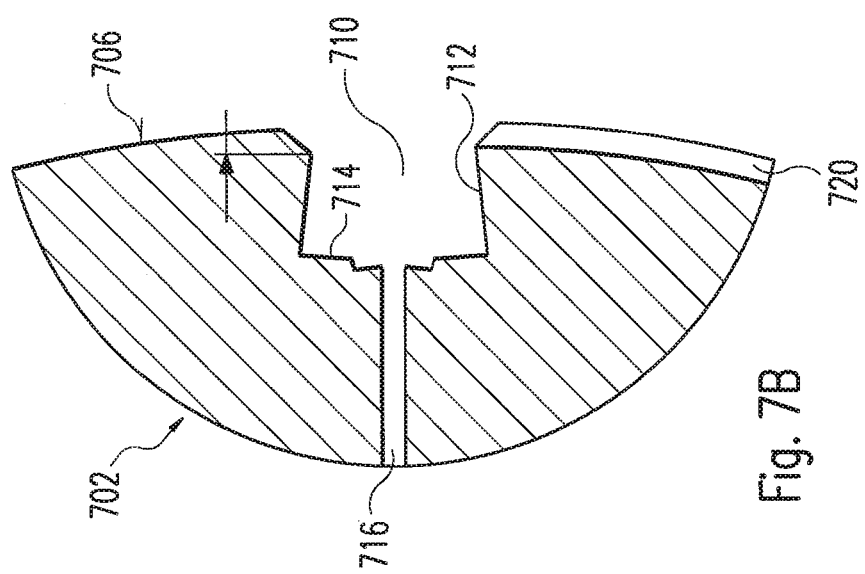

COATED HEMI-PROSTHESIS IMPLANT

CROSS-REFERENCES TO RELATED APPLICATIONS

This application claims the benefit under 35 U.S.C. § 119(a)-(b) and 35 U.S.C. § 365(a)-(b) to International Patent Application No. PCT/EP2014/074865 (published as WO 2015/096938 A1), which was filed on Nov. 18, 2014, and to German Patent Application No. 10 2013 227 136.0, which was filed on Dec. 23, 2013. Both of those applications are hereby incorporated by reference herein in their entireties.

TECHNICAL FIELD

This disclosure relates to a hemi-prosthesis implant, an implant set comprising a hemi-prosthesis implant, and a method for the manufacture of a hemi-prosthesis implant.

BACKGROUND

Implants are artificial, that is, non-natural, structures that are implanted into a human or animal body, for example, in order to replace a joint entirely or partially in the form of an endoprosthesis. The affected joints can be, for example, a shoulder, hip, knee, or ankle joint.

A joint comprises two bone ends, that is, joint halves, which face one another in a movable manner with the respective joint or tribological faces. In the case of ball joints, such as the shoulder joint or hip joint, one joint part has a concave tribological face, for example the glenoid in the shoulder joint or the acetabulum in the hip joint, while the other tribological face of the tribological pairing, for example, the humerus head or upper-arm head in the case of the shoulder joint, or the femur head or thigh-bone head in the case of the hip joint, is embodied in a convex manner.

With regard to a joint replacement, there is a distinction between a total prosthesis and a hemi-prosthesis. A total prosthesis replaces the entire joint; that is, each of the two joint halves is replaced by an implant, wherein the implant is anchored in the remaining bone. The tribological pairing between the convex and concave replacement-joint parts is mediated exclusively by artificial materials.

A hemi-prosthesis replaces only one joint half, generally the convex tribological partner. By comparison with a total prosthesis, the intervention is less serious and the stress on the patient is reduced. A hemi-prosthesis can be selected, for example, if the cartilage of the natural, concave tribological face of the glenoid, acetabulum, or tibial plateau in the knee, etc. is healthy and intact. For example, in the case of the hip joint, with a damaged femur head or fractured neck of the femur, both parts of the femur bone are replaced, but, with regard to the pelvis side, the acetabulum is retained.

Replacement joint parts must be sufficiently strong to transfer the forces acting on the joints in the long-term. Accordingly, implants in this region are often manufactured from metal or ceramic. However, in the case of hemi-prostheses there is the problem that strong prosthesis materials are not good frictional partners for the natural cartilage of the other joint half. Accordingly, it is known that, for example, steel or cobalt alloys cause damage which can go as far as destroying the cartilage.

Various materials which can be used as tribological partners for the cartilage instead of metal or ceramic have been suggested. So far, results relating to their actual suitability are available only for a few of these materials. However, the materials can be categorized by comparison with metal or ceramic roughly into rigid or hard, on one hand, or less rigid or less hard materials. Examples of hard materials include, for example, oxide-ceramic coated metals, such as oxidized zirconium, oxidized ceramic, pyrolytic carbon (pyrocarbon).

Examples of materials tending to be less rigid include various synthetic materials. At least some of these materials are not strong enough to be used as base materials for the manufacture of implants such as replacement joint parts. A corresponding implant must therefore be built up in two parts, that is, it must comprise a strong material with a coating made from a cartilage-sparing material. However, how a rigid substrate material can be joined permanently and inseparably with a less rigid coating material with regard to the forces acting in a joint remains problematic.

It is known from EP 2 086 471 B1 that a pyrocarbon shell can be fixed onto a metallic carrier. In this context, a polyethylene intermediate layer is provided. The pyrocarbon shell is embodied with a bottom edge directed inwards, which engages in a corresponding peripheral recess of the polyethylene intermediate layer, thereby providing a compression fit. The polyethylene casing and the metallic carrier each provides a corresponding peripheral groove in which an annular holding ring is retained. This arrangement can be suitable for the attachment of rigid materials such as pyrocarbon but cannot be transferred to other, less rigid materials.

SUMMARY OF THE DISCLOSURE

According to one embodiment, a hemi-prosthesis implant comprises a replacement joint part with an articulation surface for tribological pairing with a joint face of a natural joint counterpart. The articulation surface comprises a coating applied to the substrate. The substrate provides a relief for the adhesion of the coating.

In some embodiments, the implant comprises the replacement joint part as a single component. This can be, for example, a one-piece prosthesis shaft embodied, for example, as a mono block, with a replacement head. In the case of other embodiments, the implant comprises one or more further components alongside the replacement joint part. For example, an implant can comprise, as the replacement joint part, a replacement head and a prosthesis shaft as further, separate components.

The articulation surface of the replacement joint part can be embodied at least in regions as convex, in order to articulate with a concave joint surface of a natural joint part or joint counterpart.

The implant, that is, the replacement joint part and/or further components, can comprise, for example, a humerus head hemi-prosthesis, a femur-head hemi-prosthesis, a femur hemi-prosthesis component, for example, a condylar joint replacement and/or meniscus replacement or a talar body hemi-prosthesis.

The substrate for the coating can be formed from a material of the base element of the replacement joint part. If the replacement joint part comprises substantially, for example, a material such as a metal or ceramic, with regard to load-bearing and/or force transmission, this material can form the substrate. In some embodiments, at least one of the following materials is used for the manufacture of the substrate: a metal, such as titanium; one or more titanium alloys; steel, especially stainless steel; one or more cobalt alloys; zirconium; one or more zirconium alloys; tantalum, one or more tantalum alloys; one or more molybdenum alloys; a ceramic, for example, an aluminium-oxide ceramic; zirconium-oxide ceramic; one or more mixed ceramics, such as aluminium-oxide zirconium oxide; or a synthetic material, for example, a reinforced synthetic material, such as a fiber-reinforced synthetic material.

The substrate can also be formed entirely or partially from a different material from that of the base element, for example, the material of an intermediate layer formed on a base element can form the substrate. The material of the intermediate layer can also be, for example, a rigid material, for example, one of the materials named above and/or another material, such as pyrocarbon. Additionally or alternatively, the material of the intermediate layer can also be a different synthetic material, such as polyethylene, for example, if an intermediate layer comprises several sub-layers.

With regard to its property as a substrate layer for a coating, the substrate can also be referred to by the following terms: base layer, foundation, under-layer, carrier, or base.

By comparison with other dimensions of the replacement joint part, the coating can form a thin layer on the substrate. The thickness of the coating can be, for example, less than 20%, or less than 10%, or less than 5% of a radius of a convex replacement-joint part. Accordingly, under some circumstances, the coating can also be regarded as a cap, a coat, a covering on the substrate, a skin, a casing, a cladding and/or a shell.

The coating can comprise one material or several materials from the following list: a thermoplastic elastomer (TPE), polycarbonate urethane (PCU), a polyolefin polymer, a UHMWPE (ultra-high molecular weight polyethylene), an XUHMWPE (cross-linked UHMWPE), a UHMWPE or XUHMWPE with one or more additives, such as vitamin E, a polyaryl ketone or respectively polyaryl ether ketone, a polyether-ketone ketone (PEKK), a hydrogel based on PVA and/or PVD.

The substrate under the coating can be structured or contoured, for example, so that the substrate provides the relief for the adhesion of the coating. Reference could also be made to a terrain or a topography of the substrate instead of a relief. The relief offers a structure for the engagement, the adhesion, or the holding for the coating. Any enlargement of the surface area of the substrate in order to achieve a stable anchoring, for example, of an injected coating or respectively cap, can be understood in the present context as a relief.

The relief can provide a structure which is lowered or recessed by comparison with a base surface. For example, the relief can comprise recesses or indentations. A depth of such recesses can be approximately comparable to or smaller than a thickness of the coating. For example, a maximum depth of the recesses of a relief can be 100% or less of a coating thickness, or 50% or less, or 30% or less, or 10% or less.

A recess or indentation in the relief can be embodied locally or punctually, for example, in the form of a groove or concavity, undercut, etc. With some embodiments, punctual indentations can be arranged according to global or large-area patterns on the articulation surface. For example, punctual indentations can be arranged in a linear manner, that is, along lines, and/or over an area forming regions with a plurality of indentations.

Additionally or alternatively, linear recesses can be formed, for example, in the form of a plurality of grooves, striations, channels, furrows or slots, optionally with undercuts. The recesses can extend locally in a rectilinear manner, wherein in the case of convex articulation surfaces, for example, large circles can be obtained around a head region of the replacement-joint part. Other recesses can provide a local curvature and can describe, for example, partial or complete circles, wavy lines etc.

Additionally or alternatively, two-dimensional recesses can be formed. For example, a plurality of recessed regions can be present. For example, rectangular, square, circular and/or half-moon shaped recessed regions can be present.

With many embodiments, the relief can provide at least two mutually crossing grooves. Crossing angles between crossing grooves can be acute, that is, can be 45° or less, and/or can be obtuse, that is, greater than 45°. In different embodiments, the relief comprises a plurality of longitudinal and transverse grooves, wherein, in each case, a longitudinal groove and a transverse groove cross at an angle of 80° or more.

As a result of regularly crossing grooves, for example, grooves and/or other types of linear indentations arranged in a mesh, a plurality of raised regions can be defined, which can be, for example, approximately square, rectangular, diamond-shaped or otherwise segment-shaped. In this manner, for example, a ribbing of the substrate can be embodied.

With given embodiments, the relief comprises one or more roughened substrate regions. A roughening can introduce an irregular pattern into the substrate. A roughening can be present in multiple regions, for example, a plurality of uniformly roughened regions can be present in a chessboard pattern, or along a large circle, etc. The roughness can be correspondingly pronounced, as described above for the depth of recesses.

In addition to or as an alternative to indentations or roughening, the relief can provide a structure which is raised or prominent by comparison with a base surface. It should be noted, that, for example, in the case of multiply structured reliefs, the definition of a base surface and therefore the definition of a structure as an indentation or a raised area can be arbitrary.

Raised regions or projections in the relief can be formed locally or punctually. For example, the relief can provide a plurality of peaks, humps, teeth, spikes, barbs, crenulations, bumps, etc. With some embodiments, punctual raised areas can be arranged according to global or large-area patterns, for example, in a linear or two-dimensional manner forming corresponding regions with a plurality of raised areas.

Additionally or alternatively, raised areas can be embodied in a linear manner, for example, in the form of local projections, overhangs, edges etc. extending in a rectilinear or curved manner. Additionally or alternatively, raised areas can be embodied in a two-dimensional manner. For example, rectangular, square, circular and/or half-moon shaped raised areas can be present.

Some embodiments of the relief comprise a plurality of raised areas arranged in a linear manner, thereby forming a plurality of rows of teeth on the substrate surface. A row of teeth can be formed, for example, by teeth, crenulations or barbs, which project above a base surface or a raised edge or other linear projection, thereby forming teeth, a knurling or notching.

In some of these embodiments, the relief provides a plurality of rows of teeth extending longitudinally; for example, such rows of teeth can extend, in the case of a spherical-segment-shaped or otherwise rounded convex articulation surface, in the direction from a top to a base disposed opposite to the top of the replacement joint head or other limit of the articulation surface. Additionally or alternatively, transversely extending rows of teeth can be provided, and the rows of teeth can extend in a zigzag shape, which cross over one another, which form an X-shape etc.

With some embodiments, at least one ventilation borehole leading into the substrate can be provided. For the ventilation boreholes, it is sufficient that they allow a passage or a penetration or escape of air or of another atmosphere which is present, for example, during the application of the coating. This can apply in general or in regions in which a lateral escape into given regions is hindered, that is, for example, in indentations, for example, in a groove. The ventilation boreholes should not be so large that they significantly reduce an adhesion surface of the substrate and/or allow a passage of an applied coating, for example, an injection molding material, into the internal region of the base body.

Boreholes can be introduced punctually, that is, for example, as cylindrical boreholes, or can be introduced with a preferred longitudinal extension, that is, for example, as a slot or groove. An elongated ventilation gap can extend, for example, along a groove, for example, at the bottom of a groove. Such a gap could substantially provide the length of the groove, or a plurality of ventilation gaps of shorter length can be introduced along the groove; additionally or alternatively, a ventilation gap can be subdivided by bridges or ribs. A plurality of circular boreholes can also be introduced along the bottom of a groove, so that the bottom of the groove is pointed at regular intervals.

Boreholes can extend into the base body. Ventilation boreholes can either terminate as blind boreholes or can be open, that is, penetrate completely through the base body, for example, by extending into a central or internal recess of the base body. Ventilation boreholes with a blind termination can extend so far until the desired ventilation effect can be achieved. Hybrid forms are conceivable, for example, a ventilation groove or gap can be provided with punctual, open boreholes, which open into a closed or open hollow cavity of the base body.

Additionally or alternatively to the ventilation boreholes, ventilation grooves which extend along the substrate can be provided. As in the case of the ventilation boreholes, it also applies for the ventilation grooves that these should be small relative to their depth, width and/or length, and, in fact, by comparison with the actual adhesion structures, such as the anchoring grooves, in order not to influence an anchoring effect, that is, an adhesion of the coating, in an undesirable manner.

Ventilation boreholes and/or grooves can be provided independently of relief structures, that is, ventilation boreholes or grooves can be provided in a substrate region of the base body of the prosthesis in which no relief is provided. Additionally or alternatively, ventilation boreholes or grooves can be aligned with relief structures such as indentations or raised structures. Accordingly, for example, ventilation grooves can be provided along an indentation, for example, ventilation grooves can lead into or respectively lead away from such indentations. However, ventilation boreholes or grooves can also be provided adjacent to projections, such as teeth.

For example, a network or pattern of individual and/or crossing ventilation grooves can be provided. For example, a pattern of ventilation boreholes and/or grooves can be provided in combination with a roughened substrate region. Alternatively or additionally, a pattern of ventilation boreholes and/or grooves can be provided in conjunction with a flat substrate region. Exemplary embodiments of hemi-prosthesis heads are also conceivable, which provide no relief, but which do provide ventilation boreholes and/or grooves. For example, a network or pattern of ventilation boreholes and/or grooves can extend over a part of the substrate or over the entire substrate which is covered by the coating; that is, the pattern can extend below and/or outside the articulation surface.

Whether ventilation boreholes and/or grooves are provided and how these are set out, can depend in individual cases upon the coating material used, upon structures of the substrate, such as the number and arrangement of grooves, teeth, etc. The purpose of use can also be taken into consideration, for example, whether a large or a small joint replacement is involved. The required anchoring effect may also be specified by a desired load-bearing capacity. Optionally, experiments may be implemented regarding which ventilation structures lead to an optimal adhesion of the coating on the substrate or respectively on the cap of the base body.

A base body which forms the substrate can provide a pedestal exposed to the exterior. With some embodiments, an at least partially peripheral anchoring groove can be embodied directly on the pedestal, which serves, for example, to anchor the casing or respectively the cap on the base body. With these or with other embodiments, an exposed pedestal region of the base body forming the substrate can be embodied with a sharp edge at the transition to the articulation surface, for example, in order to minimize a joint gap at the outer or exposed limit between the cap and the base body.

The substrate on which a relief, a ventilation borehole, etc. can be embodied comprises the entire substrate on which a coating, cap, etc. can be or is embodied. Accordingly, the substrate can comprise a surface of the prosthesis base body which is disposed below the articulation surface but can also comprise surface regions of the base body which are not disposed below the articulation surface but alongside or outside it. The formulation used here that a relief might be disposed "outside" the articulation surface is understood to mean that the surface of the coating or cap disposed above a relief is not, or at least not during normal joint movements, disposed in contact with a joint counterpart (for example, cartilage) but is in contact, for example, with the bone or surrounding tissue surrounding a prosthesis shaft. In general, the coating or cap provides a surface which is larger or includes more than the articulation surface; this means that, in general, the substrate is also larger than the (normal) articulation surface.

With some embodiments, a relief is embodied only on the substrate or on substrate regions below the articulation surface. With other embodiments, the relief extends over a substrate region which is not disposed under the articulation surface. For example, substrate regions can provide a relief or several reliefs below and alongside the articulation surface. In many of these embodiments, the relief can be disposed alongside the articulation surface to a substantial extent.

For example, in the case of a base body embodied in a substantially spherical shape, the relief can leave a substrate region at the top free, that is to say, there is no relief under a central region of the articulation surface. With another example, a region above an equator can be left free, that is, there is no relief in a region which does not belong to the articulation zone in normal movement processes.

With some embodiments, no relief is present below the articulation surface, that is, the substrate provided by the prosthesis body is flat there, and a relief is disposed exclusively outside the (normal) articulation zone, that is, outside the zone which is articulated directly against the (natural) joint counterpart, such as cartilage, during the normal movement range of the joint. For example, in the case of a femur head, this would be the zone below the equator, that is, in the direction towards the prosthesis shaft; for example, in the case of a humerus head, this would be the flat face pointing towards the resected humerus.

How large the area is and/or in which region a relief is applied, can depend, for example, upon the adhesive effect to be achieved. Below the articulation surface, for example, a relief can be omitted completely or in part if the anchoring of the cap achievable with the remaining relief is adequate. In the case of embodiments in which a relief below the articulation surface is omitted in its entirety or partially, a relief may comprise only a pedestal region of the base body, a region such as an edge or groove in which the cap is to engage, etc.

In one approach, an adequate adhesive effect can be achieved with a ventilation by means of corresponding ventilation boreholes and/or grooves, so that a relief does not extend over the entire substrate beneath and/or outside an articulation zone. In this context, ventilation boreholes and/or grooves can be provided either in the region of the articulation zone, even if no relief is present there, and/or ventilation boreholes and/or grooves can be provided in regions outside the articulation zone, for example, in a region where the relief is present, that is, together with the relief, and/or in a region where no relief is present.

Some of the embodiments mentioned offer options for minimizing a deviation of the substrate from a target geometry in the region of the articulation surface. Dispensing with a relief below the articulation surface entirely or partially can be advantageous, for example, dependent upon a material used for the coating, if, injection faults, such as sinking points, the occurrence of which could lead to deviations from the target geometry of the articulation surface, can be avoided in this manner.

A deviation from a target geometry may also be required, for example, for safety reasons, for example, in view of legal provisions or at the request of a medical supervisory authority, for example, for any joint replacement or for a joint replacement with particularly heavy loading, for example, in the hip or knee region. The requirement may be that the base body presents no rough or rasp-like surface, also in the event of an accident, overloading, etc. and/or a potentially occurring failure of the coating, but provides a smooth face as an auxiliary articulation surface.

According to one embodiment, a hemi-prosthesis implant comprises a replacement joint part with an articulation surface for tribological pairing with a joint face of a natural joint counterpart, wherein the articulation surface is embodied with a coating applied to a substrate and at least one ventilation feature leading into or extending in the substrate is provided. The ventilation feature may be, for example, a borehole or groove, either of which can be embodied in a region of the substrate below the articulation surface. Additionally or alternatively, a ventilation feature can be embodied in a region of the substrate outside the articulation surface. With regard to embodiments of such hemi-prosthesis implants without a relief but with ventilation features, the present descriptions of example embodiments with relief and with ventilation feature(s) shall apply by analogy where applicable.

Furthermore, according to one embodiment, an implant group or implant set is proposed. The implant set comprises an implant base for holding a replacement joint part. The set further comprises a total prosthesis implant with a first replacement joint part and a second replacement joint part. Both replacement-joint parts provide, respectively, an articulation surface for tribological pairing with the other articulation surface. The set further comprises a hemi-prosthesis implant with a third replacement joint part as outlined above or described elsewhere in the present document. The first and also the third replacement joint part are provided for holding on the implant base.

The implant set can provide a modular implant system, by means of which it is possible to decide, for example, intraoperatively, whether a total prosthesis or a hemi-prosthesis should be implanted. For a total prosthesis, the first replacement joint part should be mounted or anchored on the implant base; for a hemi-prosthesis, the third replacement joint part should be mounted on the implant base.

The implant base can comprise, for example, a prosthesis shaft and/or another anchoring in a bone. Additionally, the implant base can provide a mounting possibility for the mounting of the first and/or third replacement joint part. One and the same mounting possibility can be provided for the alternative mounting either of the first or of the third replacement joint part. The mounting can be provided, for example, for plug-connection, for twist-connection, or for screw-connection of the first or third replacement joint part in the implant base.

Furthermore, a method for the manufacture of a hemi-prosthesis implant is proposed herein. The method comprises the provision of a relief on a substrate of a replacement joint part for the adhesion of a coating. A further step comprises the application of the coating for the embodiment of an articulation surface of the replacement joint part for tribological pairing with a joint surface of the natural joint counterpart.

During the manufacture of the replacement-joint part, the relief can be introduced into the substrate, for example, during the processing of a material. Additionally or alternatively, a replacement joint part can be manufactured without relief, and a relief can be introduced in a downstream step.

For the introduction of the relief, per se known techniques for metal processing can be used, if the replacement joint part provides a coating substrate made from metal, a metal alloy, etc. For example, a retrospective introduction of relief structures such as grooves can be implemented by milling. The introduction of a roughening can be implemented by means of blasting methods and/or in a chemical manner. If the coating substrate comprises a ceramic, a relief can preferably be introduced already during the manufacture of the replacement joint part, for example, during a casting process, by modelling, etc.

For the embodiment of the coating, a material such as a TPE can be applied to the substrate provided with a relief, for example, in an injection molding process. The material can be present, for example, initially in a pourable form, in order to fill up the relief, that is, for example, to flow around raised portions or to flow into indentations. After this, the material can harden and, in this manner, can embody the coating, for example, in the form of a cap or a casing on the base body of the replacement joint part. With some embodiments, a base body on which the substrate is embodied, can be used as an insert in an injection molding process.

Additionally or alternatively to injection molding processes, other methods can be used. For example, coating material can be sprayed or sintered onto the substrate, the replacement joint part can be immersed in a bath with coating material, etc. A cap or a casing or similar structure can also initially be manufactured separately for the coating and can then be attached to the substrate, for example, by means of clamping, fixing, gluing, etc.

According to different embodiments, an implant for hemi-prostheses is provided, in which a base body is formed from a rigid material. The base body made from rigid material can mediate a force transmission such as can occur in a joint. The base body can provide a substrate, onto which a less rigid material is applied in order to form an articulation surface, which can have a better biocompatibility than the rigid material of the base body. This configuration offers the possibility to use as the coating material a material which is in fact less strong but more compatible than the material of the rigid base body. A biocompatibility may comprise, for example, tribological properties and/or a biological compatibility with tissue, such as cartilage, occurring naturally in the body of a human or animal. The biocompatibility can have the effect that a cartilage of a joint surface of a natural joint is preserved longer and/or provides an increased degree of health, intactness, etc. than if the articulation surface were to be formed by the material of the base body.

With different embodiments, the material forming the articulation surface can be applied to the base body as a coating. The coating should be attached as securely and permanently as possible to the base body which bears the load. For this purpose, a relief is provided on the coating substrate, which serves for an improved adhesion of the coating on the substrate, and, in fact, by comparison with an adhesion on a substrate without relief.

The relief can form an engagement structure, a gripping structure, or a holding structure which is especially optimized for the adhesion of a comparatively less rigid material, for example, which cannot be attached or cannot be attached reliably and/or cannot be attached adequately by a compression seating or snug-fit. Relief structures should offer an overall holding, for example, to a cap formed by the coating, so that the latter is permanently secured against displacement or slipping. However, in this context, engaging excessively strongly in the less rigid coating material should be avoided in order to prevent local damage.

With a sufficiently hard material, a single nail, pin or tooth, or an individual peripheral edge, groove or fitting, for example, could be adequate to achieve an attachment. According to embodiments of the invention, two-dimensional holding structures can be provided in the case of less hard or rigid material, which, however, avoid a local overstressing of the material in order to minimize the risk of tearing, piercing, crack formation, etc. in the long-term and, in this manner, to achieve a permanent long-term and secure fitting of the coating without loosening over the course of time.

According to some embodiments, the occurrence of mechanical stresses in the coating, which can occur in the case of a differently pronounced adhesion of the coating on the substrate, can be minimized. According to different embodiments, reliefs covering the articulation surface can realize different balances between two-dimensional covering with relief structures such as teeth or grooves, on the one hand, and the local stressing of the coating by these structures. Accordingly, a permanent and secure fitting of the coating on the base body can be optimized for different coating materials, base-body materials, replacement joint types, purposes of use of the prosthesis for sports people, older people, etc.

The risk of a slipping or displacement of the coating or respectively cap occurring in the long-term and/or during given joint movements can be minimized through appropriate embodiments of reliefs, which offer, for example, a hold against forces occurring tangentially to the substrate, independently of the directions in which these forces act. For example, a relief can minimize the danger of slipping tangentially relative to the substrate in the longitudinal direction and/or in the transverse direction.

According to some embodiments, a relief can be formed by structures such as teeth and/or grooves, wherein an individual structure is embodied in such a manner that, by comparison with the overall relief, it absorbs a small force, that is, that a single such structure cannot prevent a movement of the cap. For example, a few teeth, which are, however, formed in a pronounced manner, can be embodied in the case of a relatively hard material, while more teeth can be embodied in the case of a softer material, which can, however, be less pronounced. Corresponding conditions can apply for embodiments of reliefs with roughening, ribbing, etc.

With some embodiments, a secure and permanent holding of the coating cap on the base body can be achieved at low cost. For example, a single coating on the base body can be sufficient so that no further layers, such as one or more intermediate layers, are required. It is sufficient to embody an appropriate relief in the coating substrate provided by the base material. This relief can be manufactured through techniques, for example, of material processing, which are per se known and can be used cost effectively. For example, known injection molding techniques can be used for the coating.

Embodiments described herein extend the possible applications for hemi-prostheses, for example, by providing hemi-prostheses with improved compatibility which are reliable in the long-term. Hemi-prostheses with biocompatible coating can also be used, for example, even in the case of a heavy or enduring stress on the joint, because the coating adheres permanently and reliably to the base body even under heavy stress.

In view of the possibilities for cost-favorable manufacture and/or the possibility for long-term retention in the body, for example, without cartilage damage necessitating a total prosthesis after a comparatively short time, the hemi-prostheses described herein can be used more widely as a cost-favorable alternative to the total prosthesis in spite of the optional additional coating. In this context, operation times are also shorter and, in general, the stresses on the patient are reduced. Accordingly, it should be taken into consideration that, if any subsequent treatment of the remaining natural joint half were still to be required, this would be a comparatively simpler initial implant and not a revision.

According to some embodiments, an implant set is provided in which a modular total joint replacement system with an implant base in the bone and joint replacement for connection with the implant base can be supplemented by a hemi-prosthesis implant which comprises a further joint replacement. For example, a modular replacement joint implant system can comprise a set of convex replacement joint parts (for example, femur head, humerus head or femoral condyles of the knee) made from metal or ceramic in various sizes for the total replacement, wherein, in each case, a corresponding convex replacement-joint part with improved biocompatibility is also available as a hemi-prosthesis for every size. In this manner, a surgeon can decide in a flexible manner, even intraoperatively, for a total replacement or partial replacement, which brings advantages for the patient, with regard to treatment costs etc.

BRIEF DESCRIPTIONS OF THE DRAWINGS

In the following, further aspects and advantages of the embodiments are described by way with reference to the following attached drawings.

FIG. 7B illustrates a detailed view of the base body according to FIG. 7A with a ventilation borehole and ventilation groove.

FIG. 7C illustrates a detailed view of the base body of FIG. 7A with an anchoring groove.

DETAILED DESCRIPTION OF EMBODIMENTS

With reference to the above-listed drawings, this section describes particular embodiments and their detailed construction and operation. The embodiments described herein are merely examples, set forth by way of illustration only and not limitation. Those skilled in the art will recognize in light of the teachings herein that there are alternatives, variations and equivalents to the example embodiments described herein. For example, other embodiments are readily possible, variations can be made to the embodiments described herein, and there may be equivalents to the components, parts, or steps that make up the described embodiments.

As one skilled in the art will appreciate in light of this disclosure, certain embodiments may be capable of achieving certain advantages, including, in some cases, providing a hemi-prosthesis in which an implant is built up from a rigid base material, but an articulation surface is formed from a less rigid material, and in which a permanent and secure joining of the less rigid material to the base material is optimized, with regard to considerations inter alia of cost.

Figure 1:
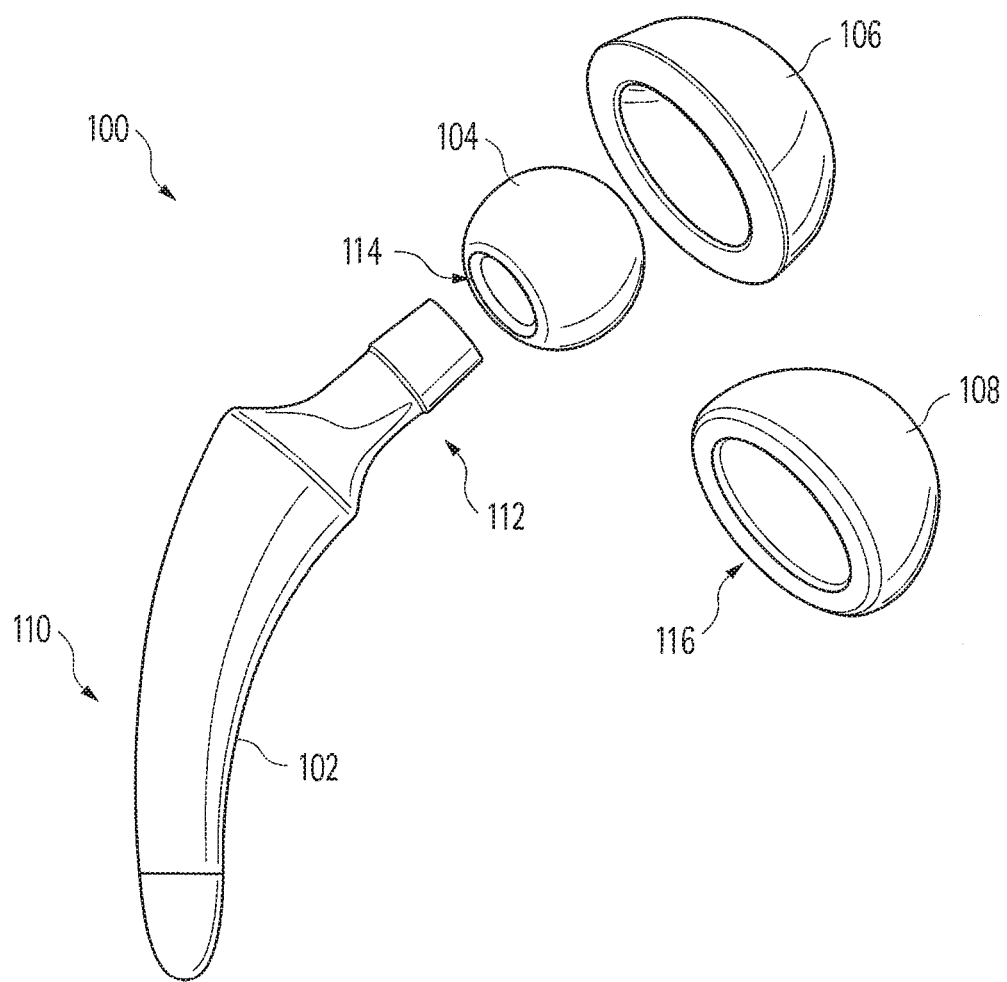
FIG. 1 illustrates, in schematic form, a modular implant set for a replacement hip joint according to a first example embodiment of the invention.

FIG. 1 shows in schematic form components of an implant set 100 for a replacement hip joint. The implant set 100 comprises an implant base, namely, a femoral shaft 102, and a convex total prosthesis part as a total prosthesis implant, namely, a total prosthesis head 104 and a concave total prosthesis part, namely a total prosthesis socket 106, and a convex hemi-prosthesis part as a hemi-prosthesis implant, namely a hemi-prosthesis head 108. The implant set 100 can comprise more than the components shown. For example, implant base, prosthesis heads and/or prosthesis sockets can be provided in different sizes; heads and/or sockets can be made from different material and/or with different coatings etc.

The hip shaft or femur shaft 102 is provided with an anchor portion 110 for anchoring in a femur bone. With the implantation of a total prosthesis, at the one end, a femoral joint head is replaced by the total prosthesis head 104 as a replacement joint part (in conjunction with the implant base 102); at the other end, an acetabulum is replaced by the total prosthesis socket 106 as the replacement joint part. For the implantation of a hemi-prosthesis, only the femoral joint head is replaced by the hemi-prosthesis head 108 (in conjunction with the implant base 102).

The implant base, that is, the femur shaft 102 can be made, for example, from a non-rusting steel, stainless steel, a metal alloy, etc. For the mounting of precisely one of the prosthesis heads 104 or 108, the femur shaft 102 comprises a mounting portion 112, which, in the example, comprises a plug-in shaft for the plug-in attachment of one of the heads 104 or 108. Each of the heads 104 and 108 provides a corresponding coupling 114 or 116 respectively. In the example, each coupling 114, 116 comprises a recess for a plug-in connection with the plug-in shaft 112 of the implant base 102. If a total prosthesis is implanted, the prosthesis head 104 is plugged on, and the replacement socket 106 is implanted in the natural, optionally correspondingly prepared acetabulum as a counterpart to the prosthesis head 104. An articulation surface of the convex replacement-joint part 104 is provided for tribological pairing with an articulation surface of the replacement-joint part 106.

If a hemi-prosthesis is implanted, the prosthesis head 108 is plugged on as a counterpart to the natural acetabulum. An articulation surface of the convex replacement-joint part 108 is provided for tribological pairing with the natural joint surface (for example, cartilage) of the natural acetabulum.

With the implant set 100, under some circumstances, it needs to be decided intraoperatively whether a hemi-prosthesis or a total prosthesis is to be implanted. For example, if the cartilage of the natural, concave tribological surface of the acetabulum is healthy and intact, a hemi-prosthesis may be adequate. If the cartilage of the acetabulum is damaged or unhealthy, a total prosthesis may be required.

As suggested in FIG. 1, the two replacement heads 104 and 106 can be different in size. For example, an outer periphery of the hemi-prosthesis 108 can, in fact, correspond with an outer periphery of the hip-socket insert 106, that is, the total prosthesis head 104 has a smaller circumference than the hemi-prosthesis head 108 because of its interplay with the total prosthesis socket 106.

The two prosthesis heads 104 and 108 can also differ in the materials used. Even if a base body of both heads 104, 108 is made from the same metal or the same ceramic, the articulation surfaces can differ. In particular, an articulation surface of the implant 108 can be coated in a cartilage-friendly manner with regard to a tribological pairing with a natural joint surface, while such a coating is not necessary for the replacement head 104. With different exemplary embodiments, for example, the running surface of the head 104 may not be further coated for the tribological pairing with the socket 106, or may be coated, for example, with a material such as polyethylene, while an articulation surface of the head 108 may be coated with PCU. This coating must be attached permanently and securely to the base body of the head 108, wherein such a base body transfers forces occurring in the hip joint and also establishes the connection to the shaft system of the prosthesis for this purpose.

Figure 2:
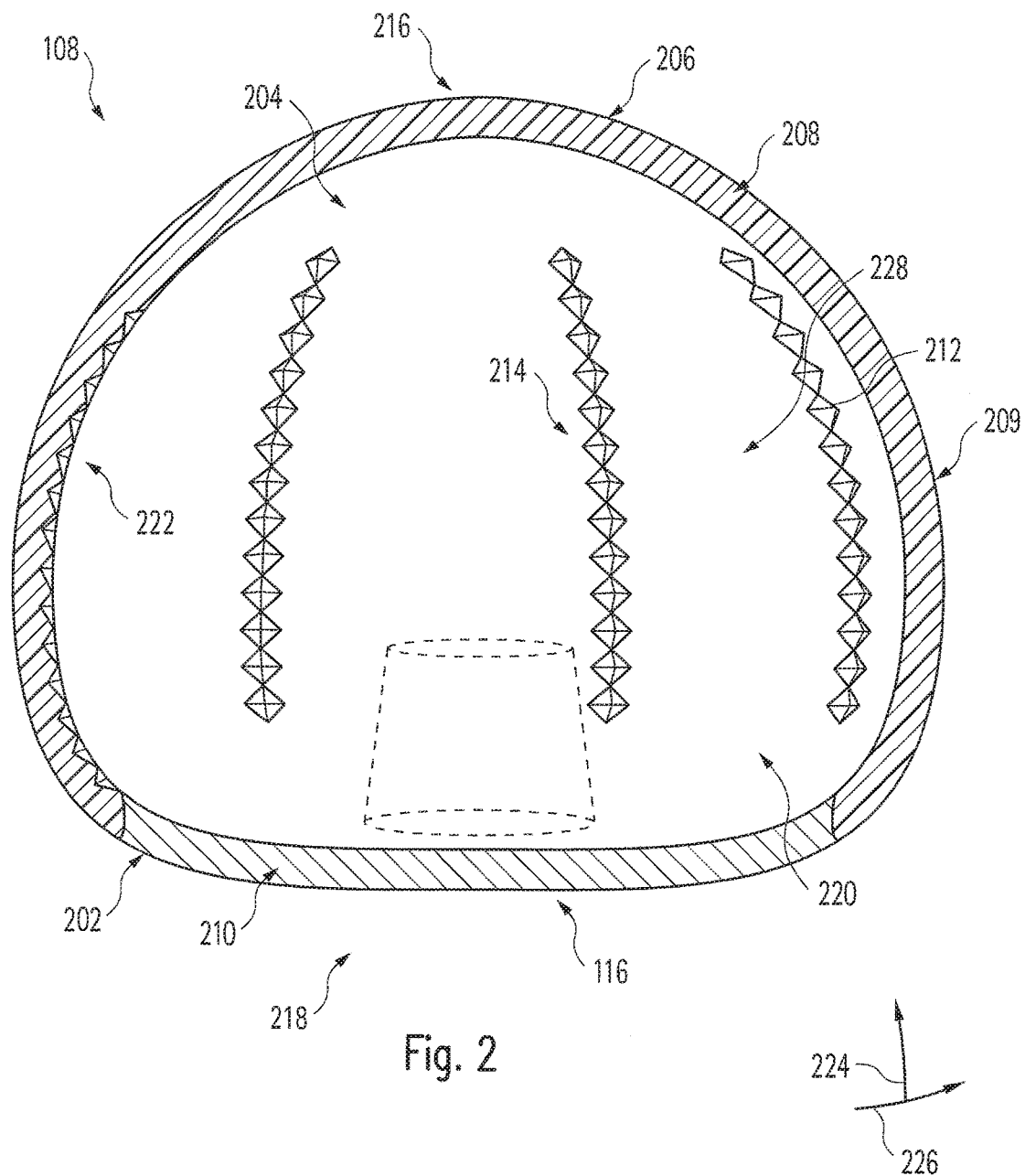
FIG. 2 illustrates in schematic, semi-transparent form, details of the femur head hemi-prosthesis from FIG. 1.

FIG. 2 shows a semi-transparent schematic view of the hemi-prosthesis head 108 from FIG. 1. A solid base body 202 comprises, for example, a metallic material such as stainless steel. The coupling element 116 in the form of a conical plug is suggested.

A surface of the base body 202 forms a substrate 204 for the actual articulation surface 206. This is provided by a coating 208 of PCU present on the substrate 204. In the hardened condition, the coating 208 in the example from FIG. 2 forms a casing or respectively a cap 209 on the base body 202, which may be metal. The cap 209 extends down to a pedestal 210 at the bottom of the base body 202. The pedestal 210 can be left free, since the articulation surface 206 for the tribological pairing with a natural acetabulum does not extend down to the pedestal 210. If the pedestal 210 can enter into an interaction with the prosthesis shaft 102 (FIG. 1), it may be advantageous to leave the pedestal free, if the interaction partners are made from the same material or material of the same hardness. By way of difference from FIG. 1, with other exemplary embodiments, a coating material can also completely cover a base body, for example, because of a generally better biocompatibility of the coating by comparison with the material of a base body.

The substrate 204 embodies a plurality of raised structures, namely teeth 212. The teeth 212 can be formed, for example, in one piece with the base body 202, or the teeth 212 can be manufactured separately (for example, in the form of rows of teeth) and, for example, introduced in such a manner into the base body 202 that they extend outwards through openings in the base surface or respectively the substrate 204. The teeth 212 are arranged in a plurality of rows 214, which extend in each case between a top 216 of the head and a bottom 218 or the pedestal 210 and are arranged at regular intervals around the periphery of the head 108. In this manner, the teeth 212 form a relief 220, which covers uniformly a large part of the substrate 204, wherein a region close to the top 216 and a region close to the bottom 218 can be excluded.

As is evident, for example, with regard to the row of teeth 222 illustrated in profile, the rows of teeth 214 engage in the coating 208. Accordingly, the less rigid cap 209, by comparison with the base body 202, is disposed not merely on a flat substrate of the more rigid base body 202, but the rows of teeth 214 allow a comparatively improved adhesion of the PCU cap 209 on the steel body 202. The rows of teeth 214 minimize tangential displacements of the cap 209 both in the longitudinal direction (arrow 224) and also in a transverse direction (arrow 226) perpendicular to the latter, and accordingly, also in combinations of such directions.

The PCU material of the cap 209 is less rigid by comparison with the force-transmitting base body 202; that is, the PCU material of the cap 209 is insufficiently rigid for a permanent transmission of forces acting in the hip joint. However, in order to achieve reliable restriction of the movement of the cap 209, not only one tooth or a few teeth are provided, but the two-dimensional relief 220 is embodied with a plurality of teeth 212 or respectively rows of teeth 214.

On the one hand, stresses within the cap 209, which could lead, for example, to the formation of cracks, can be minimized as a result. On the other hand, each individual tooth 212 or each individual row of teeth 214 must absorb only a small part of the force acting tangentially to the substrate 204, so that a loosening, wearing out etc. of the relatively soft material of the cap 209 around a tooth 212 or row of teeth 214 can be minimized, and accordingly, consequences, such as an increased mobility of the cap, a formation of cracks at the positions of the teeth 214, etc. can be avoided. Too few teeth and/or excessively pronounced teeth can lead to a piercing, tearing or other local overstressing of the cap material.

In this manner, the relief 220 can contribute to a permanent and reliable attachment of the cap 209 to the base body 202. With different exemplary embodiments, for example, rows of teeth in the transverse direction, crossing rows of teeth, etc. can also be provided alongside rows of teeth in the longitudinal direction. Corresponding reliefs can be embodied, for example, dependent upon the coating material and/or base-body material used, the type of joint or respectively anticipated stresses on the replacement joint, anticipated joint movements and intensities of movement and so on.

Additionally or alternatively to teeth or respectively rows of teeth, other relief-like structures may be present. For example, the relief 220 could be supplemented in two-dimensional regions 228 between the rows of teeth 214 through roughening or ribbing in order to further improve an adhesion of the cap 209. However, reliefs formed from only one structural element, such as teeth, may be more cost favorable to manufacture. Instead of or in addition to teeth, for example, spikes of conical or cylindrical shape or barbs with two edges can be provided. Teeth could be provided, for example, with different polyhedral shapes, for example, with three, four or more edges.

The shape and the depth of individual structural elements can also be adapted to the circumstances of the intended application. On the one hand, the teeth 212 should be sufficiently large to guarantee an adhesion of the cap 209, but not so large that there is a risk of piercing of the coating 208. A maximum projection of the teeth 212 above a base level of the substrate 204, as defined by a tooth-free region of the substrate 204 may therefore be a fraction of the thickness of the coating 208, for example, the teeth can have a maximum height of 70% or less, 50% or less, or 30% or less of the thickness of the coating 208.

Teeth of different size and/or depth can be used in one and the same relief. For example, teeth close to the top and/or the bottom of a replacement ball-joint head can be formed smaller than in a central region.

Other exemplary embodiments of implant sets, for example, for hip prostheses, are not embodied in a modular manner but contain a total prosthesis embodied in one piece as a femur shaft with head, for example, a mono-block femur shaft with joint head, and, in addition, at least one replacement hip socket, and a hemi-prosthesis embodied in one piece as a femur shaft with head, for example, also a mono-block femur shaft with a joint head. Optionally, individual components or all of these components are present in different sizes. The properties of the hemi-prosthesis in the head region can correspond to those described above for the modular head system 108, apart from the fact that the coupling 218 is dispensed with.

Figure 3:
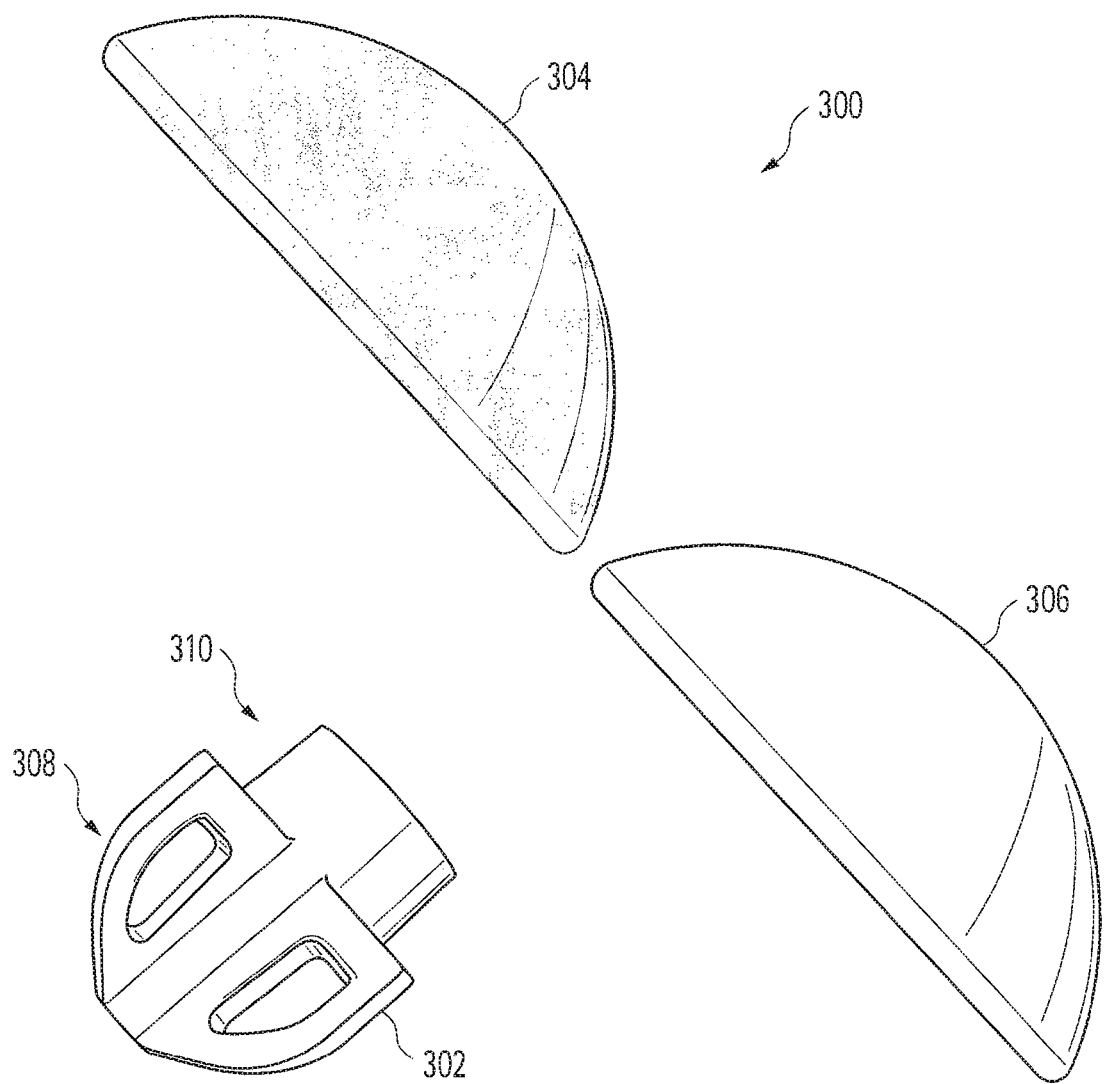
FIG. 3 illustrates in schematic form, a modular implant set for a replacement shoulder joint according to a second example embodiment of the invention.

FIG. 3 shows in schematic form components of an implant set 300 for a replacement shoulder joint. The implant set 300 comprises an implant base, namely a short humerus shaft 302, and a convex total prosthesis part, namely a total prosthesis head 304, as a total prosthesis implant, with which a concave total prosthesis part not illustrated here, namely a total prosthesis shoulder socket, is associated as a replacement shoulder socket/glenoid. The implant set 300 further comprises a convex hemi-prosthesis part, namely a hemi-prosthesis humerus head 306 as a hemi-prosthesis implant. The implant set 300 can comprise more than the components shown, for example, the shaft, prosthesis heads and/or prosthesis sockets can be provided in different sizes, made from different materials and so on.

The short humerus shaft 302 is provided for anchoring in the humerus bone by means of an anchor region 308 with bone fenestration. For the implantation of a total prosthesis, inter alia, a humerus joint head is replaced by the total prosthesis head 304. For the implantation of a hemi-prosthesis, the humerus joint head is replaced by the hemi-prosthesis head 306.

The humerus shaft 302 can comprise, for example, a metal, such as titanium, a titanium alloy, etc. Optionally, a coating can be provided, for example, on the anchor 308, which promotes a secure anchoring in the bone through bone growth. For the holding of precisely one of the prosthesis heads 304 or 306, the shaft 302 comprises a holding portion 310, which provides, for example, a plug-in shaft for the plug-in connection of one of the heads 304 or 306. If a total prosthesis is implanted, the prosthesis head 304 is plugged onto the shaft and a glenoid replacement-joint part is implanted as a counterpart. If a hemi-prosthesis is implanted, the prosthesis head 306 is plugged in as a counterpart to the natural glenoid.

With the implant set 100, under some circumstances, it needs to be decided intraoperatively whether a hemi-prosthesis or a total prosthesis is to be placed. For example, if the cartilage of the natural, concave tribological surface of the glenoid is healthy and intact, a hemi-prosthesis may be sufficient. If the glenoid cartilage is damaged or unhealthy, a total prosthesis may be required.

Accordingly, an articulation surface of the replacement-joint part 304 is adapted to a tribological pairing with an articulation surface of the glenoid replacement-joint part. An articulation surface of the convex replacement-joint part 306 is provided for a tribological pairing with the natural joint surface (for example, cartilage) of the natural glenoid.

The two prosthesis heads 304, 306 can differ in constituents or materials, with regard to the presence and composition of coatings, etc. Even if the base body of both heads 304 and 306 is made from the same basic material, such as a metal or ceramic, the articulation surfaces can be formed from different materials. In one exemplary embodiment, the running surface of the implant 304 has no further coating, while the articulation surface of the head 306 is formed by a coating. The coating of the head 306 can comprise, for example, PCU and should be attached in an inseparable manner to the base body of the head 306 which bears the load and makes the connection to the shaft system 302 of the prosthesis.

Figure 4:
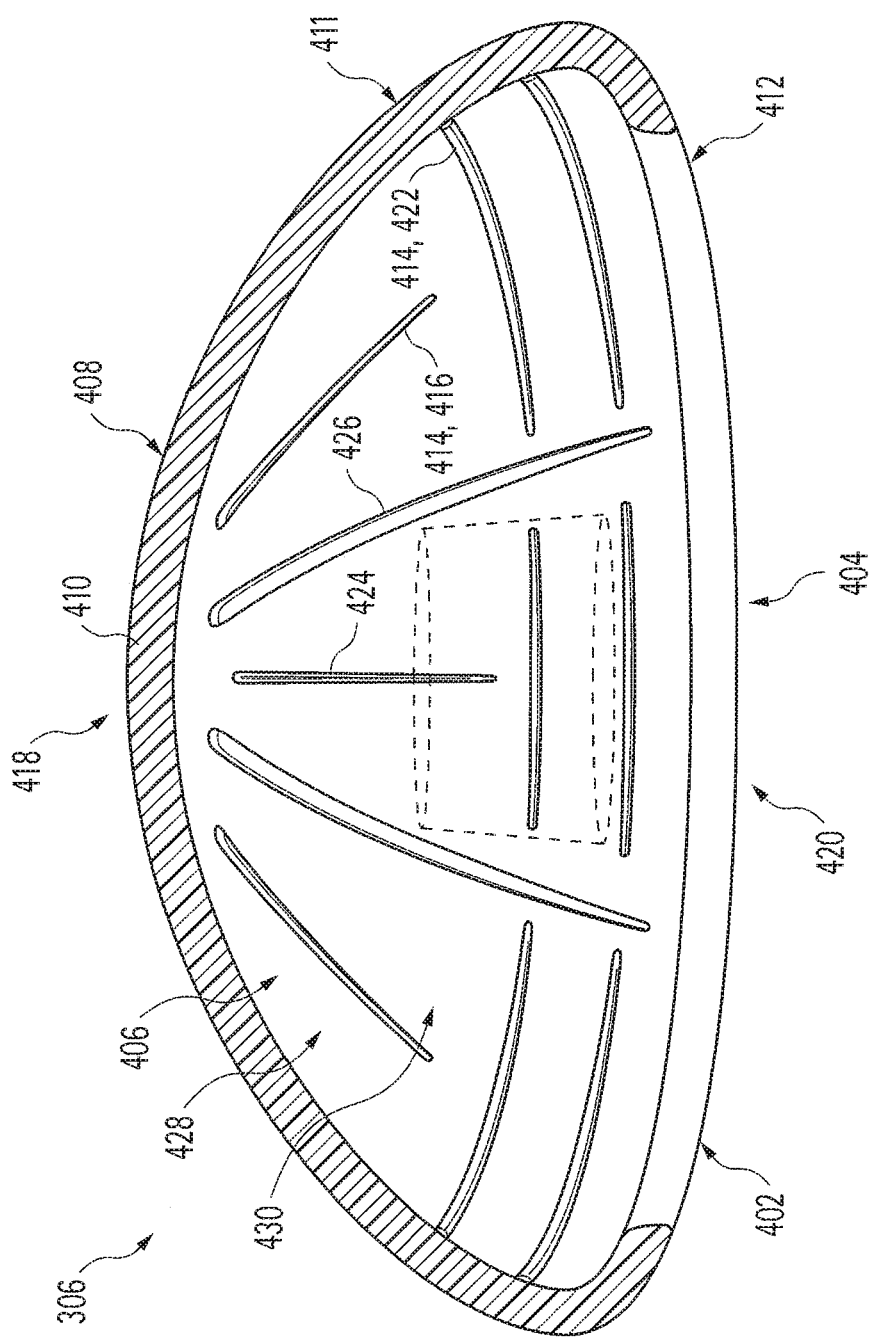
FIG. 4 illustrates in schematic, semi-transparent form, details of the humerus head hemi-prosthesis from FIG. 3.
Figure 4B:
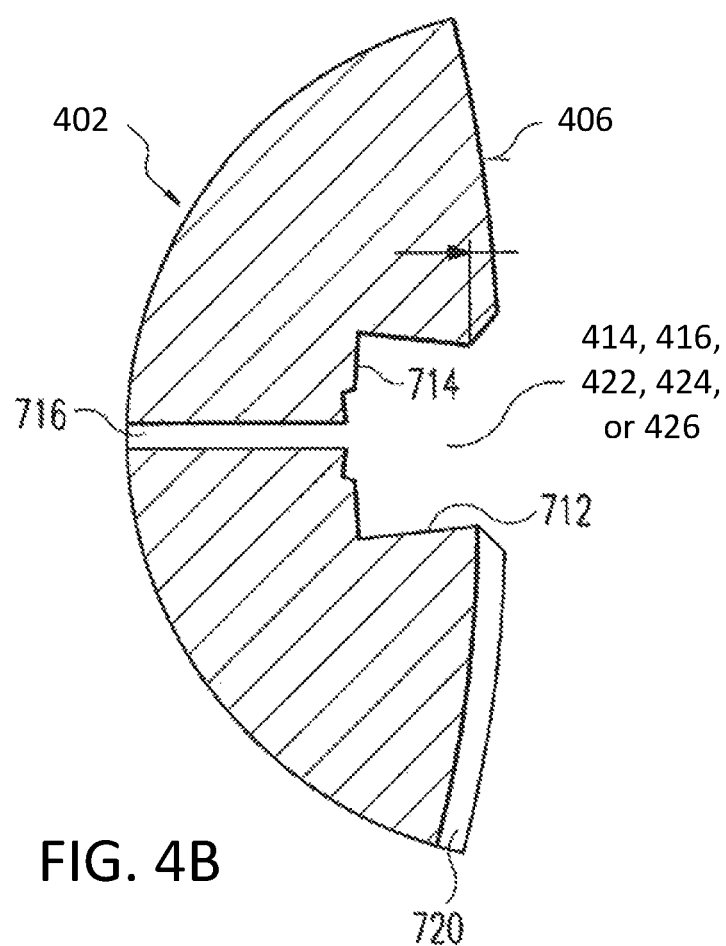

FIG. 4 is a semi-transparent schematic presentation of the hemi-prosthesis head 306 from FIG. 3. A solid base body 402 comprises, for example, a ceramic material. The coupling element 404 in the form of a plug-in cone serves for the coupling with the shaft 302.

A surface of the base body 402 forms a substrate 406 for the actual articulation surface 408. The latter is provided by a coating 410 made of PCU present on the substrate 406. In the example of FIG. 4, in the hardened condition, the coating 410 forms a casing or a cap 411 on the ceramic body 402. The cap 411 can completely cover an upper side or outer surface of the body 402 and can engage under an underside of the head 306, on which the coupling 404 is disposed. In particular, the cap 411 can extend down to a back-cut pedestal 412.

The substrate 406 embodies a plurality of grooves 414 (anchoring grooves). On the one hand, longitudinal grooves 416 are provided, which extend between a top 418 of the head and a base 420 respectively the pedestal 412 and are arranged at regular intervals around the periphery of the head 306. Furthermore, transverse grooves 422 are provided, which extend along from the peripheral lines approximately in a region close to the base 420.

Longer longitudinal grooves 426 and shorter longitudinal grooves 424 are provided. The transverse grooves 422 do not extend around the entire head 306 but are interrupted or respectively extend between the longitudinal grooves 426. In this manner, the grooves 414 form a relief 428 which covers the substrate 406. The relief 428 is more or less pronounced in different locations, since the transverse grooves 414 are preferably present close to the substrate 420.

The cap 411 formed by the coating 410 is disposed not only on the substrate 406 but engages in the groove 414 of the base body 402. Accordingly, the cap 411, which is less rigid by comparison with the base body 402, is disposed not only on a locally flat substrate of the relatively more rigid base body 402, but the grooves 414 allow an improved adhesion of the PCU cap 411 on the ceramic body 402 by comparison. The longitudinal grooves 416 minimize transverse displacements of the cap 411, and the transverse grooves 422 minimize longitudinal displacements of the cap 411 and thus improve the holding of the cap 411.

The PCU material of the cap 411 is less rigid or respectively softer and more flexible by comparison with the force-transmitting base body 402. However, in order to achieve a reliable restriction of the movement of the cap 411, it is advantageous to provide not only one single longitudinal groove and/or a single transverse groove (or a few punctual indentations) in the substrate 406, but rather a two-dimensional relief, as suggested by way of example with the relief 428 in FIG. 4.

On the one hand, stresses within the cap 411, which could lead to the formation of cracks as a result of movements of parts of the cap 411 against one another, can be minimized by the relief 428. On the other hand, each individual rib (or respectively edge, comb) of the coating 410 which engages in a groove 414, must take up only a small part of a force acting tangentially to the substrate 406, so that a loosening or wearing out of the material of the cap 411 in the region of the grooves can be minimized. Too few and/or excessively pronounced grooves can lead to local differences in the rigidity of the coating 410 and consequently to the formation of cracks or other local over-stressing of the cap.

In this manner, the relief 428 can contribute to a permanent and reliable attachment of the cap 411 on the base body 402. Additionally or as an alternative to grooves, other relief-like structures can also be present. For example, the relief 428 could be supplemented by roughened, two-dimensional regions 430 between the grooves 414, in order further to improve an adhesion of the cap 411.

The grooves 414 should be deep enough to guarantee an adhesion of the cap 411. A maximum depth of the grooves below a base level of the substrate 406, as defined locally, for example, by a groove-free region of the substrate 406, can therefore constitute a fraction of the thickness of the coating 410. For example, the grooves can have a maximum depth of approximately 70% or less, 50% or less, or 30% or less than the thickness of the coating 410.

A profile of the grooves can be embodied dependent upon the material of the substrate 406, the coating 410 and/or other circumstances in the individual case. For example, the grooves can be provided in triangular, rectangular, trough-like and/or other shapes. The depth, profile and/or number of the grooves can also be varied. For example, by comparison with a given configuration, a larger number of grooves can be provided, which are, however, flatter in order to achieve a specified adhesion effect. If very many mutually crossing grooves are provided, a relief with ribbing is achieved, as will be discussed by way of example below.

With some exemplary embodiments, more transverse grooves can be provided than suggested in FIG. 4; the additional transverse grooves could extend, for example, closer to a top of the base body. With other exemplary embodiments, more longitudinal grooves could be provided. The transverse grooves 414 in FIG. 4 are provided with interruptions at the positions of the longitudinal grooves 426. Interruptions could also be provided in the longitudinal grooves. Instead of providing only longitudinal grooves and/or transverse grooves, grooves with other orientations could also be provided additionally or alternatively, for example, diagonal grooves. Grooves could also cross one another without interruptions. A relief with crossing grooves is described below.

Other exemplary embodiments of an implant set for shoulder prostheses are not embodied in a modular manner but contain a total prosthesis embodied in one piece as a humerus shaft with a head, for example, a mono-block shoulder-shaft system with humerus head, and, in addition, at least one glenoid replacement, and a hemi-prosthesis embodied in one piece as a humerus shaft with a head, for example, also a mono-block shoulder-shaft system with a humerus head. Optionally, individual components or all of these components may be present in different sizes. The properties of the hemi-prosthesis in the head region can correspond to those which were described above for the modular-system head 306, apart from the fact that the coupling 404 is absent.

Figure 5:
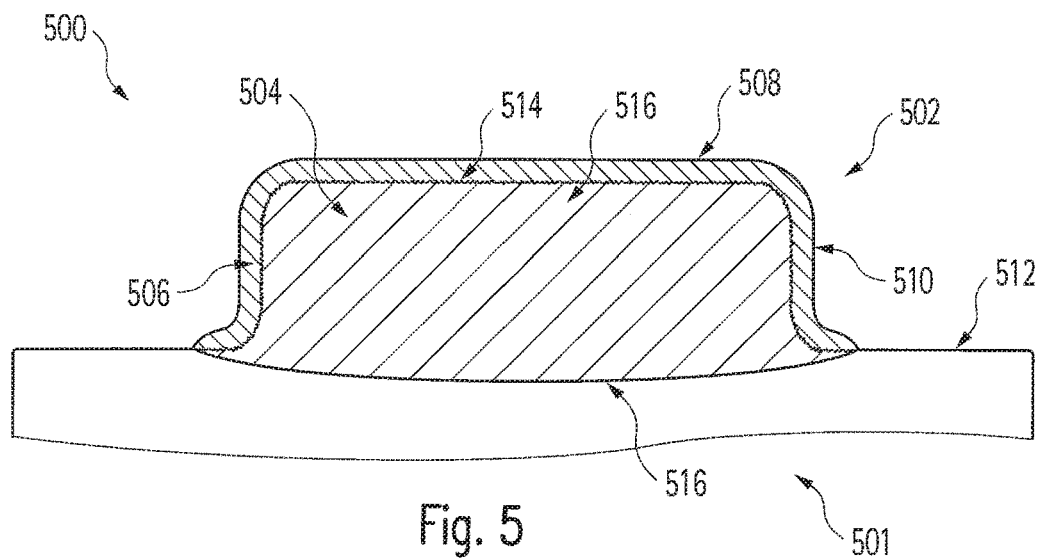
FIG. 5 illustrates in schematic, semi-transparent form, details of a femur hemi-prosthesis component according to a third example embodiment of the invention

FIG. 5 shows in a schematic semi-transparent partial view, an implant 500 for use as a femur or respectively condyle joint replacement in the form of a hemi-prosthesis. The implant 500 can be, for example, a part of an implant set for knee prostheses, wherein the set could also comprise, for example, a total prosthesis alongside the hemi-prosthesis 500.

The implant 500 comprises a base body 501 with a condyle replacement or respectively a joint knuckle 502. The condyle 502 can be solid and can be embodied, for example, in stainless steel. In the following, the base body 501 and joint condyle 502 are occasionally equated. A surface of the condyle 502 forms a substrate 504 for a cartilage-friendly coating 506, which can comprise, for example, PCU. The coating 506 forms an articulation surface 508 for articulation with a joint surface of a natural femur.

The coating 506 forms a casing or respectively a cap 510 on the condyle 502, wherein the cap 510 completely covers an outer surface of the condyle 502. With other embodiments, the coating 506 can also cover further surface regions 512 of the base body 501.

The substrate 504 is formed by a roughened surface which is suggested in FIG. 5 by an irregular contour line 514 and hatching 516 and, in this example, covers the entire condyle 502. Accordingly, the cap 510 is not disposed on a locally flat substrate, but is disposed in engagement with the roughened surface of the body 502, so that an improved adhesion of the cap 510 on the condyle 502 is guaranteed in this manner.

The rough substrate 504 minimizes displacements of the cap 510 resulting from the effects of tangential forces relative to the substrate 504. The roughening 514, 516 is a further example 518 for a two-dimensional relief which is appropriate for absorbing and transferring tangential forces locally in different regions of the articulation surface 508, and, in this manner, minimizing, on the one hand, undesirable movements or displacements of the cap 510 and, on the other hand, minimizing the occurrence of cracks or other damage to the coating 506.

By contrast with the image in FIG. 5, only partial regions of a condyle, a head or another component may be roughened for the tribological pairing. The indentations and raised areas of the relief 518 or respectively of the roughening 514, 516 should be sufficiently pronounced in order to guarantee an improved adhesion of the cap 510 by comparison with a flat substrate. The maximal raised areas or respectively indentations can range within the order of magnitude of fractions of a thickness of the coating and can be, for example, 70% or less, 50% or less, or 30% or less of a thickness of the coating 506.

Figure 6A:
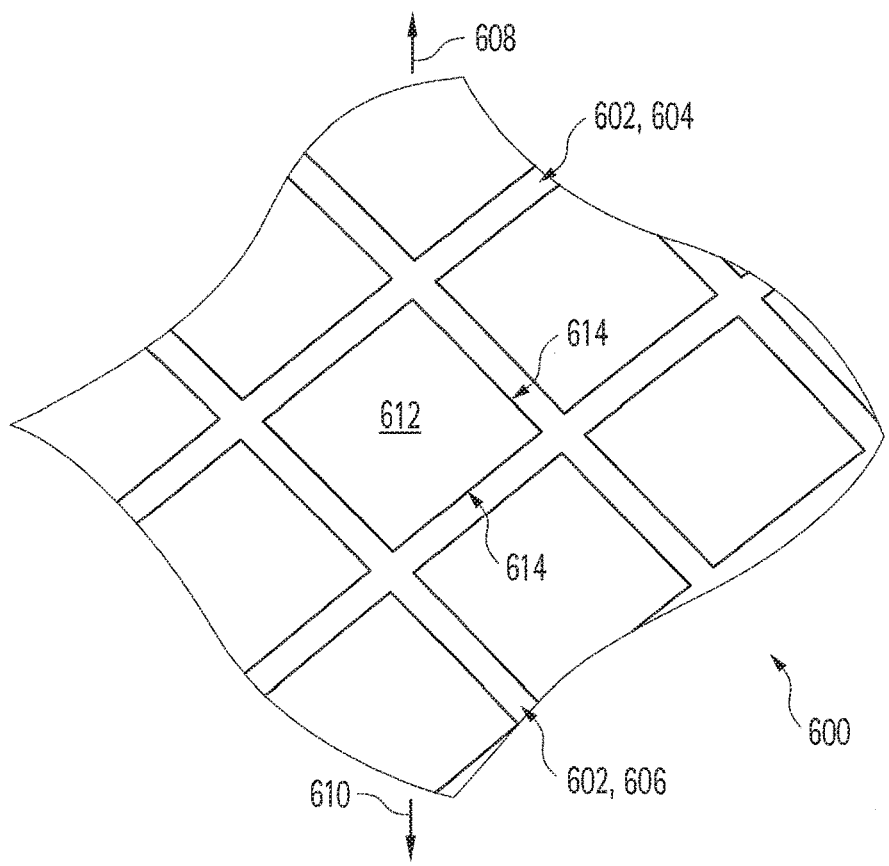
FIG. 6A illustrates in plan view, a relief according to a fourth example embodiment of the invention.

FIG. 6A shows schematically a plan view of the detail of a relief 600, as could be stamped into or onto or on a substrate of the hemi-prosthesis implant in order to optimize an adhesion for a coating for the embodiment of an articulation surface. In the exemplary embodiment of FIG. 4, the relief 428 comprises a plurality of grooves 414 embodied without crossings. In the exemplary embodiment of FIG. 6A, by contrast, the relief 600 comprises a plurality of mutually crossing grooves 602. In the case of parallel grooves 604, for example, these could be longitudinal grooves, and in the case of parallel grooves 606, these could be transverse grooves. However, the grooves 604, 606 can also run in other directions, for example, in diagonal directions relative to a top or a bottom, for example, of a convex replacement-joint part, wherein the direction towards the top or respectively bottom is indicated by arrows 608 or respectively 610.

For the embodiment of the grooves 602, the same applies as discussed for the grooves 412 of FIG. 4. The grooves 602 define raised regions 612, of which the edges 614 lead to a restriction of movement in the event of tangential forces acting on an attached coating and accordingly an improved adhesion of the coating on the substrate. As shown by the example in FIG. 6A, the relief 600 can be described, on the one hand, as a patterning determined by the grooves 602, wherein the grooves 602 are indentations relative to a base surface or respectively an imagined flat substrate. However, this description is arbitrary because, on the other hand, the relief 600 can also be described as a pattern of raised regions 612. Which form of description is selected can be made dependent, for example, upon manufacturing, for example, if the relief 600 is generated by the introduction of grooves 602. However, other approaches are also conceivable.

Figure 6B:
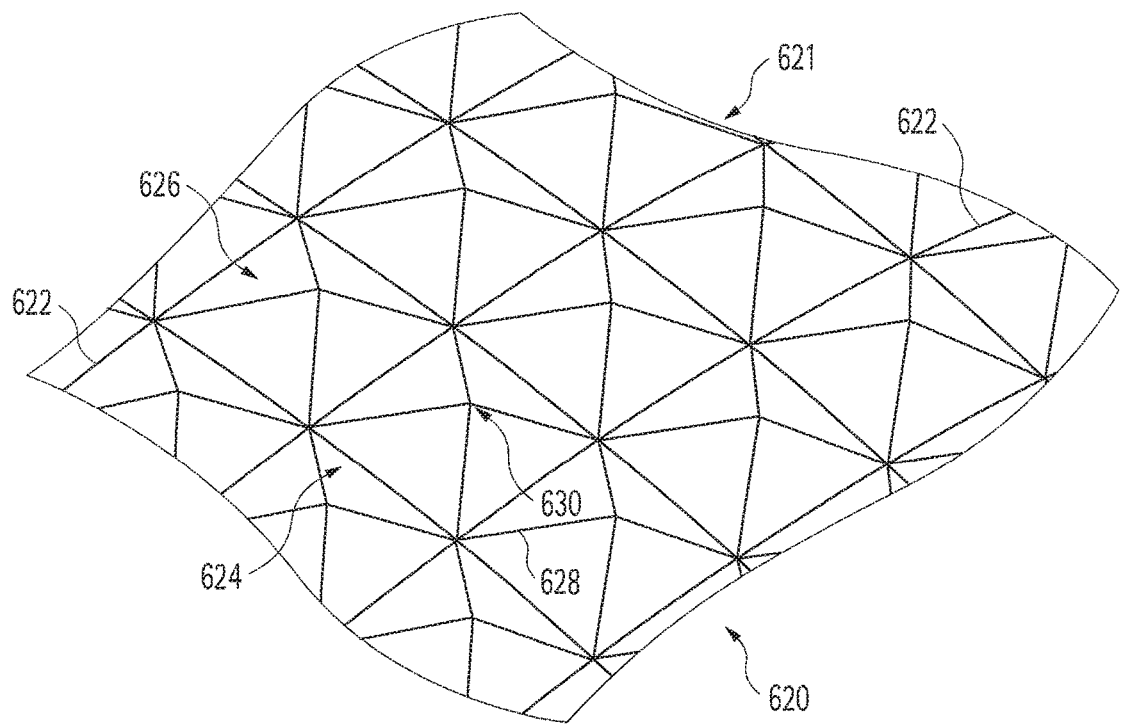
FIG. 6B illustrates in plan view, a relief according to a fifth example embodiment of the invention.

FIG. 6B shows schematically a detail in plan view of a further exemplary embodiment of a relief 620. The latter comprises a ribbing 621 for the improvement of an adhesion of the coating. The ribbing 621 comprises a plurality of grooves, channels or corrugations 622 which define a plurality of raised regions 624. Each of these regions forms a tooth 626. Each tooth has four edges or ridges 628 and a tip 630. Other designs, for example, other polyhedral shapes with fewer or more edges are also conceivable.

Figure 6C:
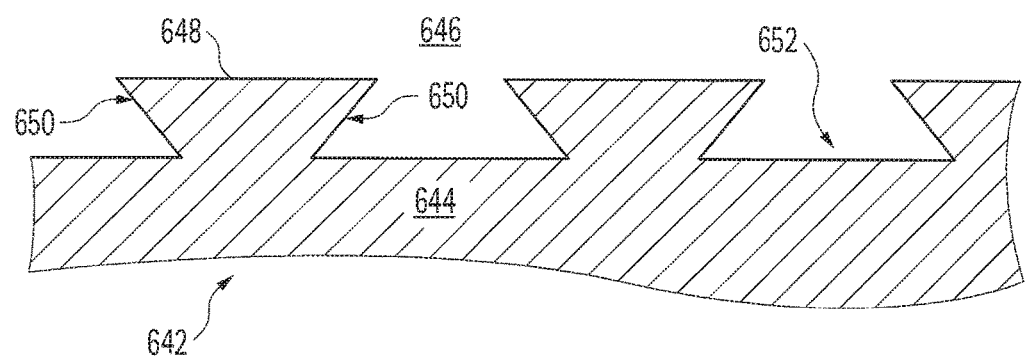
FIG. 6C illustrates in profile view, a relief according to a sixth example embodiment of the invention.

FIG. 6C shows a schematic cross-section through a substrate 642 which is formed by a surface of a base body 644, and in which a plurality of raised regions 648 are embodied for the improved adhesion of a coating 646. The raised regions 648 each provide two hook-like structures 650 in a region facing towards the coating 646. The hooks 650 can be embodied on both sides as shown, or also only on one side.

According to a complementary description of the configuration of FIG. 6C, grooves, channels or indentations 652 are introduced into the substrate 642, wherein the grooves 652 provide overhanging edges. Structures such as those shown in FIG. 6C could be introduced into a metallic base body, for example, by milling metal processing or into a ceramic base body by means of ceramic casting.

Figure 7A:
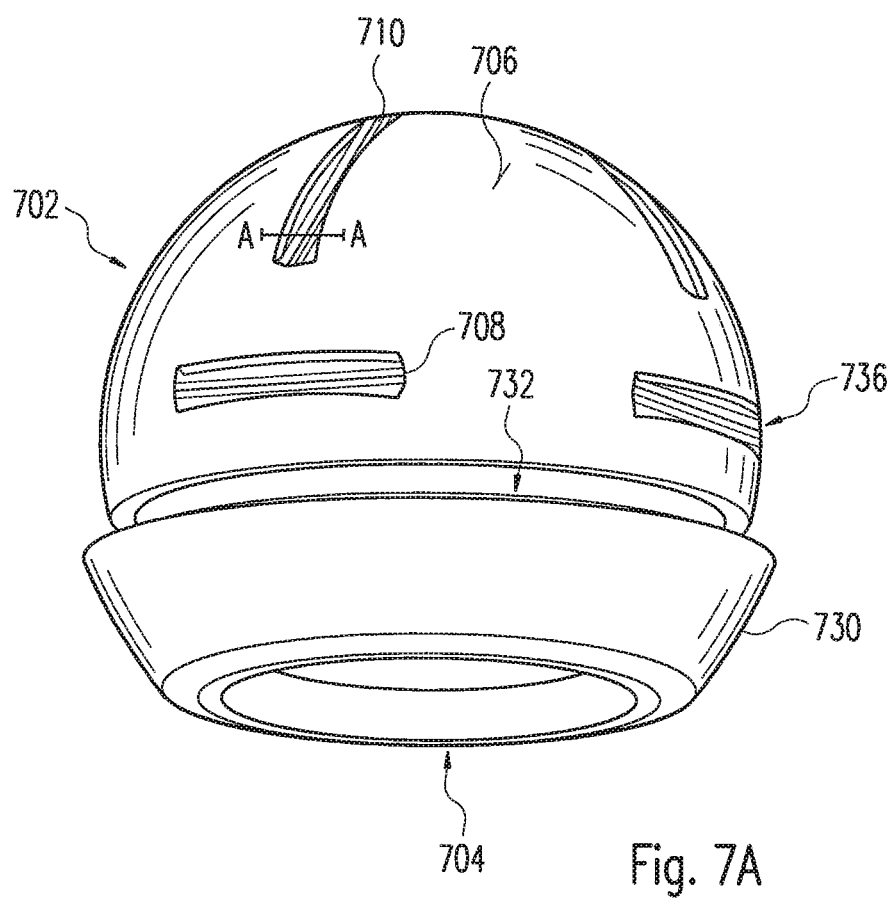
FIG. 7A illustrates a prosthesis base body of a seventh example embodiment of the invention.

FIG. 7A shows an exemplary embodiment of a base body 702 for a hemi-prosthesis head, wherein the coating or respectively cap or casing have been omitted here. For a hemi-prosthesis head for which the base body 702 could be used, the discussion with reference to the prosthesis head 108 of FIGS. 1 and 2 applies by analogy.

The base body 702 can be embodied from a metallic material, such as steel. A coupling element in the form of a conical plug 704 is suggested. A surface of the base body 702 forms a substrate 706 for a coating to be applied. The substrate 706 embodies a plurality of grooves 708. Unless otherwise stated, the description discussed, for example, with reference to the grooves 414 of the exemplary embodiment of FIG. 4 also applies for these grooves 708 by analogy.

FIG. 7B shows a cross-sectional profile through the base body 702 with the grooves 710 along the line A-A in FIG. 7A. The groove 710 is introduced into the base body 702 with lateral walls 712 and a base 714. The lateral walls 712 can be embodied as undercuts, that is, with overhanging edges, as was described with reference to FIG. 6C. A borehole 716 is introduced into the bottom 714 of the groove 712, which can extend continuously through to an internal region of the base body 702. For example, the borehole 716 can open into the cone 704, which is shown in FIG. 7A.

During the course of manufacture of the hemi-prosthesis 700, the substrate 706 is coated with a synthetic material, for example, in an injection molding process. In this context, the base body 702 can be used as a metallic insert component. During the course of injection over the substrate 706 with the synthetic material, the borehole 716 serves for ventilation. This can, for example, improve the adhesion of the resulting coating or respectively cap.

As indicated in FIG. 7B, an area of the substrate 706 occupied by a ventilation borehole 716 can, in general, be considerably smaller than an area occupied by an indentation, such as the groove 710 or respectively its bottom 714. Ventilation boreholes, channels or openings can be, for example, less than 50%, less than 30%, less than 20% or less than 10% of the bottom area of the groove or other indentation.

The ventilation borehole 716 leads perpendicularly away from the substrate 706 or respectively the base 714 of the groove 710 into the interior of the base body 702, that is, at an angle of 90° to the local surface 706, 714 of the base body 702. With other exemplary embodiments, the borehole can also extend diagonally, that is, with an angle different from 90°, that is, for example, with an angle of 80° or 70°. This can be advantageous, for example, so that a borehole can reach an interior hollow cavity of the base body.

Furthermore, a ventilation groove 720 is indicated in FIG. 7B, which is introduced into the substrate 702, and, in fact, starting from the groove 710 and leading away from the latter. The groove 720 also serves for the ventilation and therefore for the attainable improved adhesion of a coating applied to the substrate 706 or respectively to the base body 702. The embodiments of the ventilation borehole 716 also apply by analogy for the ventilation groove 720 where applicable.

Ventilation grooves can lead perpendicularly, that is, at an angle of 90°, from a groove, such as the groove 710, or can lead away at a different angle, for example, 75° or 45°. Ventilation grooves can be short, so that a length of the ventilation groove is, for example, shorter than or equal to the width or the depth of the indentation, for example, a groove, to be ventilated. However, ventilation grooves can also be long and can extend over a multiple of the width of an indentation to be ventilated. In the case of given exemplary embodiment, a ventilation groove can connect several structures to be ventilated to one another, such as several grooves, for example, the grooves 708 in FIG. 7A.

Several ventilation boreholes and/or grooves can be provided for each structure to be ventilated. For example, 3 ventilation grooves or 10 ventilation grooves can be provided on each side of the groove 710 in FIG. 7A.

Ventilation boreholes, such as the borehole 716, can be arranged in an indentation, for example, of a groove, like the groove 710 in FIG. 7B, in grooves 602 in FIG. 6A, in channels 622 as in FIG. 6B and so on. Similarly, ventilation grooves can lead away from such indentations.

FIG. 7A shows that the coating substrate 706 is provided adjoining a pedestal 730 of the base body 702 with a peripheral anchoring groove 732.

FIG. 7C shows a further cross-sectional profile through the base body 702, wherein the profile intersects the pedestal 730 and the anchoring groove 732. The groove 732 can be provided dependent upon the coating material used, in order to optimize an anchoring of the coating or respectively of the casing formed by the coating on the base body 702. A depth 734 of the groove 732 and/or further design parameters can be established dependent upon the coating material, purpose of use, that is, upon the type of prosthesis and the forces transmitted etc.

The groove 732 is shown in FIG. 7A as peripheral, however, modifications are possible; for example, an anchoring groove may be embodied only in parts or segments. Instead of one complete or partial peripheral anchoring groove, several (transverse) anchoring grooves can be provided parallel to one another, wherein the transition to transverse grooves 736 can extend in a flowing manner.

In principle, it is conceivable for an anchoring groove to be provided with a spacing distance relative to a pedestal region of the base body; however, for the present, if an anchoring groove is regarded as expedient, the configuration shown in FIGS. 7A and 7C, in which the anchoring groove 732 is provided directly on the pedestal 730, is preferred. This minimizes a joint gap at the transition 738, which can occur between the base body 702 and respectively the outer surface 740 of the pedestal 730, on the one hand, and an applied coating, on the other hand, wherein, after the application, the coating forms a cap 742 as indicated by the dashed line. The cap 742 can be formed, for example, from an injection molded PCU material.

In order to minimize a joint gap at the transition 738 from the PCU tribological surface 744 of the cap 742 to the metallic pedestal exterior 740 gap, the outer edge or corner 746 of the pedestal undercut 748 of the pedestal 712 can be embodied with sharp edges, and the pedestal edge 748 can otherwise extend in a straight line without structuring in the direction towards the substrate 706 or respectively the groove 732. In this manner, a flush mounting, for example, of injection-molded material on the pedestal edge 748 can be facilitated. If the edge 746 were to be embodied in a rounded manner, it can occur that the injection molded material used does not wet up to the outer edge of the pedestal accurately. In such cases, an indentation or trough could be formed, for example, at the transition between synthetic material surface and metal surface.

Figure 8:
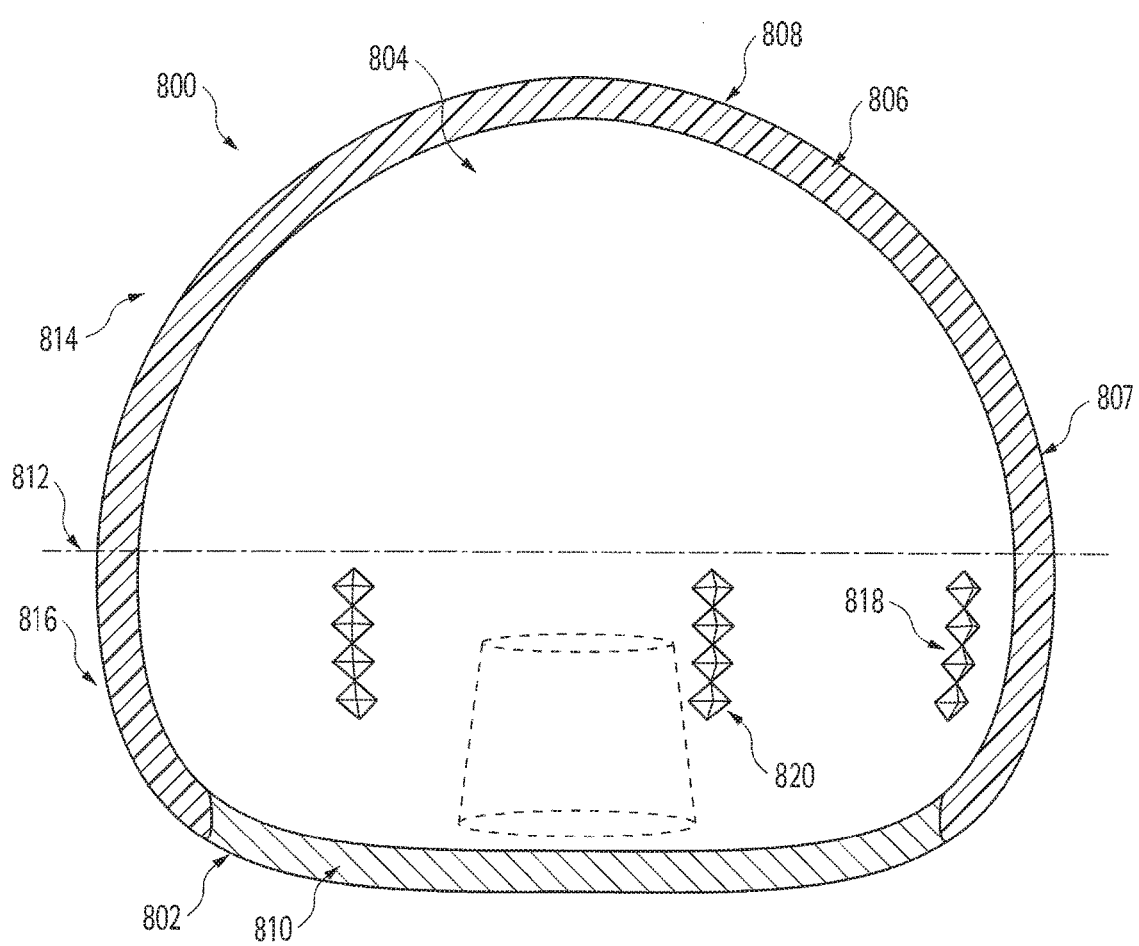
FIG. 8 illustrates a prosthesis head with base body and coating of an eighth example embodiment of the invention.

FIG. 8 shows a view of a hemi-prosthesis head 800 which can be a variation of the prosthesis head 108 of FIG. 2; such aspects, in which the two heads 108 and 800 can be identical, will not be described explicitly again in the following.

A base body 802 offers a substrate 804 for a coating 806 or cap 807, on which or by which the articulation surface 808 is formed. Expressed more accurately, the cap 807 covers the base body 802, wherein the cap 807 extends down to a pedestal 810 of the head 800. Without the pedestal 810, the head 802 has an approximately spherical shape, so that a surface of the cap 807 also assumes a spherical shape.

FIG. 8 indicates an equator 812, wherein the term "equator" relates to the approximately spherical shape of the cap 807, as is known to the person skilled in the art. The surface of the cap 807 in a region 814 above the equator 812 represents the actual articulation surface 808, that is, in the case of normal joint movements, the region 814 provides the articulating zone or respectively the articulation region interacting with the (natural) joint counterpart. Under normal movement conditions, a region 816 below the equator 812 does not belong to the articulating zone 808.

The substrate 804 embodies a plurality of teeth 818, as was described in detail for the exemplary embodiment of FIG. 2 with teeth 212. In the example in FIG. 8, the teeth 818 are also arranged in a plurality of rows of teeth 820. However, by way of difference from the exemplary embodiment of FIG. 2, the rows of teeth 820 are provided only outside the normal articulation zone 814, that is, in the region 816 adjoining the pedestal 810, while, in the region 814, that is, below the articulation zone 808, the substrate 804 is free from teeth or other relief structures, that is, the substrate 804 is flat below the articulation surface 808.

An adhesion or respectively anchoring effect of the cap 807 on the base body 802 achieved with the rows of teeth 820 can be sufficient so that a relief below the articulation surface is not required. Conversely, if an absence of a relief below the articulation zone 808 is required, for example, for safety reasons, an adequate adhesive affect can still be achieved, as shown by the example of FIG. 8. Optional additional measures to be taken, for example, the provision of ventilation boreholes or grooves to facilitate the expulsion of air during an injection molding of the coating 806, thereby achieving an improved adhesive effect, have not been shown in the drawing.

The humerus head 306 from FIG. 4 could also be modified in such a manner that the grooves 414 below the articulation surface 408 can be omitted in their entirety or in part. For example, a relief could be provided outside the articulation surface 408 in a region 432 (compare FIG. 4). The area 432 faces towards the (remaining, resected) humerus and extends down to the backwardly offset pedestal 412, which adjoins the prosthesis shaft 310, (compare FIG. 2). The area 432 provides the substrate for the cap 411 in a region in which the cap 411 engages around the outer edge 434 of the base body 402, which limits the articulation surface 408.

For example, longitudinal grooves and/or transverse grooves can be provided in the region 432 (not visible in FIG. 4), for which the same description applies by analogy with regard to their embodiment, extension etc., as was described explicitly for the grooves 414, 416, 422 shown in FIG. 4. For an improvement of the adhesive effect, it is also conceivable to provide ventilation boreholes and/or grooves, and, in fact, either in the articulation region 408, even if a relief has not been provided there, or in the region 432, or in both regions 408 and 432.

Figure 9:
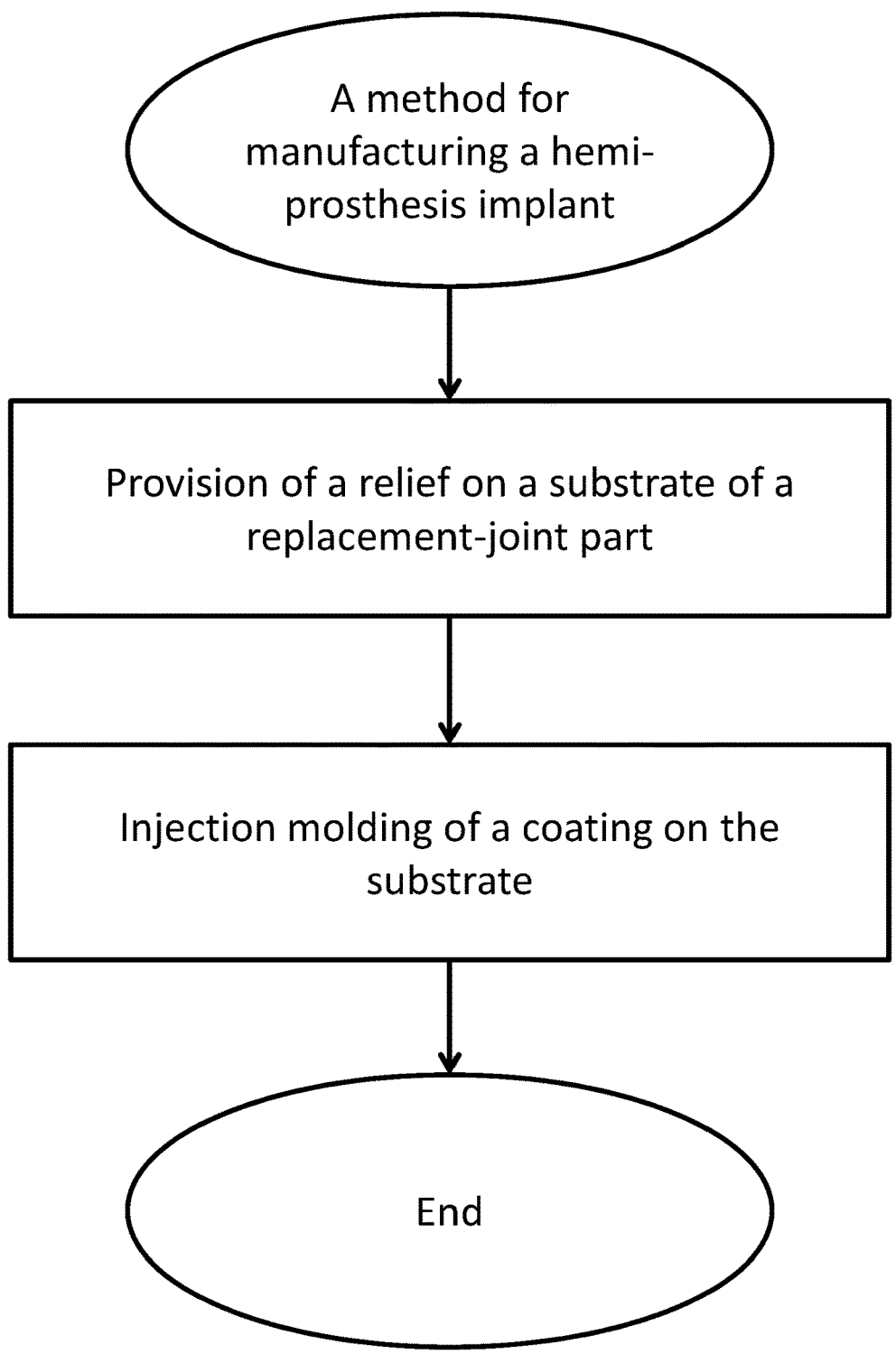
FIG. 9 illustrates in the form of a flow diagram, the course of a method for the manufacture of a hemi-prosthesis implant according to one embodiment of the invention.

FIG. 9 shows a flow chart with an exemplary embodiment of a method 900 for the manufacture of a hemi-prosthesis implant. In step 902, a relief is provided on a substrate of a replacement-joint part for the improved adhesion of a coating to be applied downstream. The relief can be provided, for example, during the manufacture of a base body of the replacement part. Accordingly, a relief structure can be embodied, for example, on or in a metallic or ceramic body by means of casting, modelling, stamping, pressing etc. Additionally or alternatively, a downstream processing can be implemented after a manufacture of a base body. For example, using chip-removing or milling processes, grooves can be introduced into a metallic body as shown in FIG. 4 or 6A. A roughened substrate, as suggested in FIG. 5, can be introduced into a metallic body using a blasting process.

In step 904, the coating is applied to the substrate which has been prepared, that is, provided with a relief. For example, a synthetic material such as a TPE, for example, PCU, can be applied to the substrate by means of injection molding. The material flows around the relief structures. After a hardening, the coating encloses raised relief structures or respectively fills indented relief structures. Accordingly, the coating adheres to the base body in a special manner.

In step 906, the method 900 is completed, for example, by integrating the manufactured hemi-prosthesis implant in an implant set. Methods such as the method 900 and modifications thereof allow a cost-favorable manufacture of coatings for strong joint replacement hemi-prostheses with biocompatible articulation surface.

The invention is not restricted to the exemplary embodiments described here and the aspects emphasized here. On the contrary, especially but not exclusively within the field indicated by the appended claims, a plurality of modifications is possible, which are disposed within the scope of activities of a person skilled in the art. In particular, given combinations of features described separately above will be evident to the person skilled in the art as expedient or advantageous.

The invention claimed is:

1. A hemi-prosthesis implant comprising:
a replacement joint part with an articulation surface for tribological pairing with a joint surface of a natural joint counterpart, wherein the articulation surface is embodied with a coating applied to a substrate, wherein the substrate provides a relief for adhesion of the coating, and wherein in an indentation of the relief one or more of a ventilation borehole located at the lowest part of the bottom of the indentation and leading into the substrate and a ventilation groove starting at the top edge of the indentation and leading away from the indentation is present.

2. A hemi-prosthesis implant according to claim 1, wherein the relief provides a plurality of grooves.

3. A hemi-prosthesis implant according to claim 2, wherein the relief provides a plurality of longitudinal grooves and transverse grooves.

4. A hemi-prosthesis implant according to claim 1, wherein the relief provides a ribbing.

5. A hemi-prosthesis implant according to claim 1, wherein the relief comprises at least one roughened substrate region.

6. A hemi-prosthesis implant according to claim 1, wherein the substrate is formed from one or more of a metal, a ceramic, and a reinforced synthetic material.

7. A hemi-prosthesis implant according to claim 1, wherein a material of the coating comprises one or more of a thermoplastic elastomer, polycarbonate urethane, a polyolefin polymer, a polyaryl ketone, and a hydrogel.

8. A hemi-prosthesis implant according to claim 1, wherein an at least partially peripheral anchoring groove is embodied directly on an outer pedestal of a base body forming the substrate.

9. A hemi-prosthesis implant according to claim 1, wherein the relief is embodied entirely or partially outside the articulation surface.

10. A hemi-prosthesis implant according to claim 1, wherein the implant comprises a humerus-head hemi-prosthesis, a femur-head hemi-prosthesis, a hemi-prosthesis femur component, or a talar-body hemi-prosthesis.

11. A hemi-prosthesis implant according to claim 1, wherein in the indentation of the relief the ventilation borehole located at the lowest part of the bottom of the indentation and leading into the substrate and the ventilation groove starting at the top edge of the indentation and leading away from the indentation are present.

12. A hemi-prosthesis implant according to claim 11, further comprising a metallic base body, wherein the substrate is on a surface of the metallic base body, and wherein the borehole located at the lowest part of the bottom of the indentation extends continuously from the indentation through the metallic base body to an internal region of the metallic base body.

13. An implant set comprising:
an implant base for holding a replacement joint part;
a total prosthesis implant with a first replacement joint part with an articulation surface for tribological pairing with an articulation surface of a second replacement joint part of the total prosthesis implant; and
a hemi-prosthesis implant with a third replacement joint part, the third replacement joint part having a third replacement joint part articulation surface for tribological pairing with a joint surface of a natural joint counterpart, wherein the third replacement joint part articulation surface is embodied with a coating applied to a substrate, and wherein the substrate provides a relief for adhesion of the coating;
wherein both the first and also the third replacement joint part are embodied for holding by the implant base, so that either a total prosthesis or hemi-prosthesis can be implanted, and
wherein in an indentation of the relief one or more of a ventilation borehole located at the lowest part of the bottom of the indentation and leading into the substrate and a ventilation groove starting at the top edge of the indentation and leading away from the indentation is present.

14. An implant set according to claim 13, further comprising a metallic base body, wherein in the indentation of the relief the ventilation borehole located at the lowest part of the bottom of the indentation and leading into the substrate and the ventilation groove starting at the top edge of the indentation and leading away from the indentation are present, wherein the substrate is on a surface of the metallic base body, and wherein the borehole located at the lowest part of the bottom of the indentation extends continuously from the indentation through the metallic base body to an internal region of the metallic base body.

15. A method for manufacturing a hemi-prosthesis implant, the method comprising:
generating a relief on a substrate of a replacement joint part for adhesion of a coating; and
injection molding of the coating for embodiment of an articulation surface of the replacement joint part for tribological pairing with a joint surface of a natural joint counterpart; and
disposing in an indentation of the relief one or more of a ventilation borehole located at the lowest part of the bottom of the indentation and leading into the substrate and a ventilation groove starting at the top edge of the indentation and leading away from the indentation.

16. A method according to claim 15, wherein the relief comprises one or more of a plurality of grooves, a plurality of teeth, a ribbing, and a roughened surface.

17. A method according to claim 15, wherein substrate is formed from one or more of a metal, a ceramic, and a reinforced synthetic material.

18. A method according to claim 15, wherein a material of the coating comprises one or more of a thermoplastic elastomer, polycarbonate urethane, a polyolefin polymer, a polyaryl ketone, and a hydrogel.

19. A method according to claim 15, wherein the hemi-prosthesis implant comprises a humerus-head hemi-prosthesis, a femur-head hemi-prosthesis, a hemi-prosthesis femur component, or a talar-body hemi-prosthesis.

20. A method according to claim 15, further comprising:
disposing in the indentation of the relief the ventilation borehole located at the lowest part of the bottom of the indentation and leading into the substrate and the ventilation groove starting at the top edge of the indentation and leading away from the indentation;
forming the substrate on a surface of the metallic base body; and
extending the borehole located at the lowest part of the bottom of the indentation continuously from the indentation through the metallic base body to an internal region of the metallic base body.

* * * * *